United States Patent
Cong et al.

(10) Patent No.: US 6,956,961 B2
(45) Date of Patent: Oct. 18, 2005

(54) EXTRACTING SHAPE INFORMATION CONTAINED IN CELL IMAGES

(75) Inventors: Ge Cong, El Cerrito, CA (US); Eugeni A. Vaisberg, Foster City, CA (US)

(73) Assignee: Cytokinetics, Inc., San Francisco, CA (US)

( * ) Notice: Subject to any disclaimer, the term of this patent is extended or adjusted under 35 U.S.C. 154(b) by 552 days.

(21) Appl. No.: 09/792,013

(22) Filed: Feb. 20, 2001

(65) Prior Publication Data

US 2002/0154798 A1 Oct. 24, 2002

(51) Int. Cl.$^7$ .................................................. G06K 9/00
(52) U.S. Cl. ....................................................... 382/133
(58) Field of Search ................................ 382/128, 131, 382/133, 134, 171, 259; 600/562; 73/61.48; 702/19, 21, 22, 23, 26, 27, 29, 30, 32, 137; 430/21, 332, 333, 334, 335, 336, 378, 398, 541, 545, 550, 616; 250/461.2; 435/1.1, 40.5

(56) References Cited

U.S. PATENT DOCUMENTS

| | | |
|---|---|---|
| 4,818,710 A | 4/1989 | Sutherland et al. |
| 4,922,092 A | 5/1990 | Rushbrooke et al. |

(Continued)

FOREIGN PATENT DOCUMENTS

| | | |
|---|---|---|
| EP | 0468705 | 1/1992 |
| EP | 0 317 139 B1 | 2/1995 |

(Continued)

OTHER PUBLICATIONS

Russ, J.C., "The Image Processing Handbook." Second Edition. Boca Raton: CRC Press. 1995. pp. 469–474 and 457–461.*

Lu et al, "Hierarchical Shape Recognition Using Polygon Approximation and Dynamic Alignment"; IEEE Paper CH2561-9, vol. 2, pp. 976–979, Apr. 1988.*

(Continued)

*Primary Examiner*—Andrew W. Johns
*Assistant Examiner*—Shervin Nakhjavan
(74) *Attorney, Agent, or Firm*—Beyer, Weaver & Thomas, LLP.

(57) ABSTRACT

Methods and apparatus are provided for the analysis of images of cells and extraction biologically-significant shape-related features from the cell images. The extracted features may be correlated with particular conditions induced by biologically-active agents with which cells have been treated, thereby enabling the automated analysis of cells based on cell shape parameters. In particular, the invention provides methods for segmentation of cells in an image using a combination of a reference component image data and cell shape-indicative marker image data in a watershed technique. Further, the invention provides a skeletonization and skeleton analysis technique for extracting biologically-relevant features from cell shapes.

24 Claims, 15 Drawing Sheets

U.S. PATENT DOCUMENTS

| | | | |
|---|---|---|---|
| 4,959,301 A | 9/1990 | Weaver et al. | |
| 4,965,725 A | 10/1990 | Rutenberg | |
| 5,016,283 A | 5/1991 | Bacus et al. | 382/129 |
| 5,162,990 A | 11/1992 | Odeyale et al. | |
| 5,163,095 A * | 11/1992 | Kosaka | 382/133 |
| RE34,214 E | 4/1993 | Carlsson et al. | |
| 5,281,517 A | 1/1994 | Bacus et al. | 435/6 |
| 5,287,272 A | 2/1994 | Rubbenberg et al. | |
| 5,326,691 A | 7/1994 | Hozier | |
| 5,355,215 A | 10/1994 | Schroeder et al. | |
| 5,526,258 A | 6/1996 | Bacus | |
| 5,548,661 A | 8/1996 | Price et al. | |
| 5,655,028 A | 8/1997 | Soll | |
| 5,710,022 A | 1/1998 | Zhu et al. | 435/69.1 |
| 5,733,721 A | 3/1998 | Hemstreet, III et al. | |
| 5,741,648 A | 4/1998 | Hemstreet et al. | |
| 5,768,412 A * | 6/1998 | Mitsuyama et al. | 382/173 |
| 5,776,748 A | 7/1998 | Singhvi et al. | |
| 5,777,888 A | 7/1998 | Rine et al. | |
| 5,790,692 A | 8/1998 | Price et al. | |
| 5,790,710 A | 8/1998 | Price et al. | |
| 5,804,436 A | 9/1998 | Okun et al. | |
| 5,856,665 A | 1/1999 | Price et al. | |
| 5,893,095 A | 4/1999 | Jain et al. | |
| 5,919,646 A | 7/1999 | Okun et al. | |
| 5,932,872 A | 8/1999 | Price | |
| 5,962,250 A | 10/1999 | Gavin et al. | |
| 5,976,825 A | 11/1999 | Hochman | |
| 5,985,549 A | 11/1999 | Singer et al. | 435/6 |
| 5,989,835 A | 11/1999 | Dunlay et al. | |
| 5,991,028 A | 11/1999 | Cabib et al. | |
| 5,995,143 A | 11/1999 | Price et al. | |
| 6,007,996 A | 12/1999 | McNamara et al. | |
| 6,008,010 A | 12/1999 | Greenberger et al. | |
| 6,078,681 A | 6/2000 | Silver | 382/133 |
| 6,083,763 A | 7/2000 | Balch | |
| 6,103,479 A | 8/2000 | Taylor | |
| 6,146,830 A | 11/2000 | Friend et al. | |
| 6,169,816 B1 * | 1/2001 | Ravkin | 382/128 |
| 6,222,093 B1 | 4/2001 | Marton et al. | |
| 6,345,115 B1 | 2/2002 | Ramm et al. | |
| 6,615,141 B1 | 9/2003 | Sabry et al. | 702/19 |
| 6,658,143 B2 * | 12/2003 | Hansen et al. | 382/133 |
| 2002/0141631 A1 | 10/2002 | Vaisberg et al. | 382/133 |
| 2002/0154798 A1 | 10/2002 | Cong et al. | 382/129 |

FOREIGN PATENT DOCUMENTS

| | | | |
|---|---|---|---|
| EP | 0902394 | 3/1999 | |
| WO | WO 87/02802 | 5/1987 | |
| WO | WO 93/21511 | 10/1993 | |
| WO | WO 94/11841 | 5/1994 | |
| WO | WO 95/10036 | 4/1995 | |
| WO | WO 95/22749 | 8/1995 | |
| WO | WO 96/01438 | 1/1996 | |
| WO | WO 96/09605 | 3/1996 | |
| WO | WO 97/11094 | 3/1997 | |
| WO | WO 97/20198 | 6/1997 | |
| WO | WO 97/40055 | 10/1997 | |
| WO | WO 97/43732 | 11/1997 | |
| WO | WO 97/45730 | 12/1997 | |
| WO | WO 98/05959 | 2/1998 | |
| WO | WO 98/35256 | 8/1998 | |
| WO | WO 98/38490 | 9/1998 | |
| WO | WO 98/44333 | 10/1998 | |
| WO | WO 98/45704 | 10/1998 | |
| WO | WO 98/52018 | 11/1998 | |
| WO | WO 99/05323 | 2/1999 | |
| WO | WO 99/08091 | 2/1999 | |
| WO | WO 99/17116 | 4/1999 | |
| WO | WO 99/39184 | 8/1999 | |
| WO | WO 99/44062 | 9/1999 | |
| WO | WO 99/54494 | 10/1999 | |
| WO | WO 99/67739 | 12/1999 | |
| WO | WO 00/03246 | 1/2000 | |
| WO | WO 00/06774 | 2/2000 | |
| WO | WO 00/17624 | 3/2000 | |
| WO | WO 00/17643 | 3/2000 | |
| WO | WO 00/17808 | 3/2000 | |
| WO | WO 00/26408 | 5/2000 | |
| WO | WO 00/29984 | 5/2000 | |
| WO | WO 00/31534 | 6/2000 | |
| WO | WO 00/33250 | 6/2000 | |
| WO | WO 00/43820 | 7/2000 | |
| WO | WO 00/49540 | 8/2000 | |
| WO | WO 00/50872 | 8/2000 | |
| WO | WO 00/60356 | 10/2000 | |
| WO | WO 00/65472 | 11/2000 | |
| WO | WO 00/70528 | 11/2000 | |
| WO | WO0135072 A2 | 5/2001 | G01N/15/14 |

OTHER PUBLICATIONS

Hartwell et al., "Integrating Genetic Approaches into the Discovery of Anticancer Drugs". Science, vol. 278, Nov. 7, 1997. XP002916842.

Ng et al., "Evaluating Multi–Dimensional Indexing Structures for Images Transformed by Principal Component Analysis". Dept. of Computer Science, University of British Colombia, Vancouver, B.C. V6T 1Z4, Canada. XP000642562.

Boland et al. "Automated Recognition of Patterns Characteristics of Subcellular Structures in Fluorescence Microscopy Images". Cytometry 33:366–375 (1998).

Rubas, et al., "An Integrated Method to Determine Epithelial Transport and Bioactivity of Oral Drug Candidates in Vitro," Pharmaceutical Research, vol. 13, No. 1, (1996) pp 23–27.

Uria JA, et al., "Regulation of Collagenase–3 Expression in Human Breast Carcinomas in Mediated by Stromal–Epithelial Cell Interactions", Cancer Res Nov. 1, 1997;57 (21):4882–8, Abstract.

Wang et al., "Immunolocalization of 6 in CHO cells with anti–His antibodies", Dec. 1999.

Cormack, Brendan P. et al., "FACS–optimized mutants of the green fluorescent protein (GFP)", 1996, Gene, vol. 173, pp. 33–38.

Craig, Elizabeth and Gross, Carol, "Is hsp70 the cellular thermometer?", 1991, TIBS, pp. 135–140.

Cubitt, Andrew B. et al., "Understanding, improving and using green flourescent proteins", 1995, TIBS, vol. 20, pp. 448–455.

Dobson, Stephen P., "Dynamics of insulin–stimulated translocation of GLUT4 in single living cells visualized using green fluorescent protein", 1996, FEBS Letters, vol. 393, pp. 179–184.

Georget, V., et al., "Trafficking of the androgen receptor in living cells with fused green fluorescent protein—androgen receptor", 1997, Molecular and Cellular Endorcrinology, vol. 129, pp. 17–26.

Lippincott–Schwartz, Jennifer and Smith, Carolyn L., "Insights into secretory and endocytic membrane traffic using green fluorescent protein chimeras", 1997, Current Opinion in Neurobiology, vol. 7, pp. 631–639.

Misteli, Tom and Spector, David L., "Applications of the green fluorescent protein in cell biology and biotechnology", 1997, Nature Biotechnology, vol. 15, pp. 961–964.

Palm, Gottfried J. et al., "The structural basis for spectral variations in green fluorescent protein", 1997, Nature Structural Biology, vol. 4, No. 5, pp. 361–365.

Sakai, Kenji et al., "Purification and characterization of N–acyl–D–glutamate deacylase from Alcaligenes xylosoxydans subsp. xylosoxydans A–6", 1991, FEBS Letters, vol. 289, No. 1, pp. 44–46.

Shulga, Nataliya et al., "In Vivo Nuclear Transport Kinetics in *Saccharamyces cerevisiae*: A Role for Heat Shock Protein 70 during Targeting and Translocation", 1996, *The Journal of Cell Biology*, vol. 135, No. 2, pp. 329–339.

Tarasova, Nadya I. et al., "Visualization of G Proteincoupled Receptor Trafficking with the Aid of the Green Fluorescent Protein", 1997, *The Journal of Biological Chemistry*, vol. 272, No. 23, Issue of Jun. 6, pp. 14817–14824.

Welsh, Stephen and Kay, Steve A., "Reporter gene expression for monitoring gene transfer", 1997, *Current Opinion in Biotechnology*, vol. 8, pp. 617–622.

Mattheakis et al., PCT Search Report for Int'l Application No. PCT/US2004/022970, Int'l Filing Date Jul. 15, 2004, dated Dec. 1, 2004.

Mattheakis et al., PCT Written Opinion for Int'l Application No. PCT/US2004/022970, Int'l Filing Date Jul. 15, 2004.

Towner et al., "Non–Invasive in Vivo Magnetic Resonance Imaging Assessment of Acute Aflatoxin B1 Hepatotoxicity in Rats", BBA—General Subjects, Elsevier Science Publishers, NL, vol. 1475, No. 3, Jul. 26, 2000, pp. 314–320.

Sturgeon et al., "In Vivo Assessment of Microcystin–LR–induced Hepatoxicity in the rat using proton nuclear magnetic rezsonance ($^1$H–NMR) Imaging" BBA—General Subjects, Biochemica et Biophysica Acta 1454 (1999) pp 227–235.

Sakai et al., Rapid and Sensitive Neurotoxicity Test Based on the Morphological Changes of PC12 Cells with Simple Computer–Assisted Image Analysis, Journal of Bioscience and Bioengineering, vol. 90, No. 1, 20–24. 2000.

Hall et al., "Two Methods of Assessment of Methotrexate Hepatotoxicity in Patients with Rheumatoid Arthritis", Annals of the Rheumatic Diseases 1991, vol. 50, No. 7, pp. 471–476.

Molinari et al., "Automated Image Analysis for Monitoring Oxidative Burst in Macrophages", Analytical and Quantitative Cytology and Histology, vol. 22, No. 5, Oct. 2000, pp423–427.

U.S. Appl. No. 60/120,801, filed Feb. 19, 1999, Wang et al.

U.S. Appl. No. 60/142,646, filed Jul. 6, 1999, Boyce et al.

U.S. Appl. No. 60/142,375, filed Jul. 6, 1999, Boyce et al.

U.S. Appl. No. 60/108,291, filed Nov. 13, 1998, Boyce et al.

U.S. Appl. No. 60/110,643, filed Dec. 1, 1998, Smith.

U.S. Appl. No. 60/140,240, filed Jun. 21, 1999, Dunlay et al.

Printout from Q3DM Website (www.Q3DM.com), printed on Mar. 1, 2001, 30 Pages.

Montironi R., et al., "Computed Cell Cycle and DNA Histogram Analyses in Image Cytometry in Breast Cancer", Journal of Clinical Pathology, GB, London, vol. 46, No. 9, Sep. 1993, pp. 795–800.

Giuliano K.A., et al., "Fluorescent–Protein Biosensors: New Tools for Drug Discovery", Trends in Biotechnology, GB, Elsevier Publications, Cambridge, vol. 16, No. 3, Mar. 1998, pp. 135–140.

Printout from Automated Cell Website (www.automatedcell.com) printed on Mar. 9, 2001, 24 Pages.

Ravi Kapur, et al., "Design and Fabrication of Spatially Controlled Miniaturized Organ Systems From Stem Cells", U.S. Provisional Appl. No.: 60/127,339, filed Apr. 1, 1999, 21 Pages.

Giuliano et al., "High–Content Screening: A New Approach to Easing Key Bottlenecks in the Drug Discovery Process", *J. Biomolecular Screening*, 2(4): 249 (1997).

Pauwels et al., "Determination of the Mechanism of Action of Anticancer Drugs by Means of the Computer– Assisted Microscope Image Analysis of Feulgen–Stained Nuclei", *J. Pharmacological and Toxicological Methods.* 37: 105–115 (1997).

Pauwels et al., "Monitoring Of Chemotherapy–Induced Morphonuclear Modifications By Means Of Digital Cell–Image Analysis", I. Cancer Res. Clin. Oncol., 119: 533–540 (1993).

Pauwels et al., "In Vitro Digital Cell Image Analysis of Morphonuclear Modifications Induced by Natural DNA—Interacting Anticancer Drugs in Three Neoplastic Cell Lines", *Meth. Find. Exp. Clin. Pharmacol..* 17(3): 151–161 (1995).

Pauwels et al., "The Application of Computerized Analysis of Nuclear Images and Multivariate Analysis to the Understanding of the Effect of Antineoplastic Agents and Their Mechanism of Action", *Meth. Find. Exp. Clin. Pharmacol,* 15(2): 113–124 (1993).

Teri Adams, et al., "Cell Patterning on Glass and Polymeric Substrates", U.S. Provisional Appl. No.: 60/138,119, filed Jun. 7, 1999, 21 Pages.

Pauwels et al., "Combination of Computerized Morphonuclear and Multivariate Analyses to Characterize In Vitro the Antineoplastic Effect of Alkylating Agents", J. Pharmacol. and Toxicol. Methods, 33(1): 34–45 (1995).

Weinstein et al., "An Information–Intensive Approach to the Molecular Pharmacology of Cancer", *Science,* 275: 43–349 (Jan. 17, 1997).

Ancin, Hakan et al., "*Advances in Automated 3–D Image Analysis of Cell Populations Imaged by Confocal Microscopy*", 1996, Cytometry, vol. 25, pp. 221–234.

Malpica, Norberto et al., "*Applying Watershed Algorithms to the Segmentation of Clustered Nuclei*", 1997, Cytometry, vol. 28, pp. 289–297.

Nilsson, Björn et al., "*Segmentation of Dense Leukocyte Clusters*", 2001, IEEE Workshop on Mathematical Methods in Biomedical Image Analysis, Kauai, Hawaii, pp. 221–227.

István Cseke, "A Fast Segmentation Scheme for White Blood Cell Images", © 1992 IEEE, pp. 530–533.

Blankenstein et al., Modular concept of a laboratory on a chip for chemical and biochemical analysis, © 1998, Biosensors & Bioelectronics, vol. 13., No. 3–4, pp. 427–438.

Hofland et al., "Role of Tumor–Derived Fibroblasts in the Growth of Primary Cultures of Human Breast–Cancer Cells: Effects of Epidermal Growth Factor and the Somatostatin Analogue Octreotide", © 1995 Wiley–Liss, Inc., Publication of the International Union Against Cancer, pp. 93–99.

Serbouti, et al., "Image Segmentation and Classification Methods To Detect Leukemias", (1991) Annual Int'l Conf. of IEEE Eng. In Medicine & Biology Soc., vol. 13, No. 1, pp. 0260–0261.

Stearns et al., Interleukin 10 (IL–10) Inhibition of Primary Human Prostate Cell–induced Angiogenesis: IL–10 Stimulation of Tissue Inhibitor of Metalloproteinase–1 and Inhibition of Matrix Metalloproteinase (MMP)–2/MMP–9 Secretion, (1999) Clin. Cancer Res. 5: 189–196.

Sundblad, et al., "The use of image analysis and automation for measuring mitotic index in apical conifer meristems", Oct. 1998, Journal of Experimental Botany, vol. 49, No. 327, pp. 1749–1756.

Takayama et al., "Patterning cells and their environments using multiple laminar fluid flows in capillary networks", (1999) Proc. Natl., Acad. Sci USA, 96:5545–5548.

* cited by examiner

551

EXTRACTING SHAPE INFORMATION CONTAINED IN CELL IMAGES

CROSS-REFERENCE TO RELATED PATENT APPLICATIONS

This application is related to the following co-pending U.S. patent applications, U.S. patent application Ser. No. 09/310,879 by Vaisberg et al., filed May 14, 1999 and titled DATABASE METHOD FOR PREDICTIVE CELLULAR BIOINFORMATICS; U.S. patent application Ser. No. 09/311,996 by Vaisberg et al., filed May 14, 1999 and titled DATABASE SYSTEM INCLUDING COMPUTER FOR PREDICTIVE CELLULAR BIOINFORMATICS; U.S. patent application Ser. No. 09/311,890 by Vaisberg et al., filed May 14, 1999 (now U.S Pat. No. 6,742,576) and titled DATABASE SYSTEM FOR PREDICTIVE CELLULAR BIOINFORMATICS; U.S. patent application Ser. No. 09/729,754 by Vaisberg et al., filed Dec. 4, 2000 and titled CLASSIFYING CELLS BASED ON INFORMATION CONTAINED IN CELL IMAGES and; U.S. patent application Ser. No. 09/792,012 (Publication No. 20020141631) by Vaisberg et al., filed concurrently herewith and titled IMAGE ANALYSIS OF THE GOLGI COMPLEX; each of which is incorporated herein by reference for all purposes.

BACKGROUND OF THE INVENTION

The present invention pertains to image analysis methods used to extract shape information from images of cells.

Cell shape is a recognized indicator of cell type and/or condition. Thus, it is possible to identify many cell types and to distinguish them from other cell types based on the cells' shapes. In addition, many interesting biological conditions may be correlated with cell shape. Biological "conditions" of interest to researchers include disease states, normal unperturbed states, quiescent states, states induced by exogenous biologically-active agents, etc. Valuable insight may be gained by inducing a biological condition through a genetic manipulation, exposure to a particular agent (e.g., a compound, radiation, a field, etc.), deprivation of required substance, and other perturbations. Such a condition may cause changes in a particular cell's shape, and the cell's modified shape may be indicative of that particular condition. In this regard, there known correlations between cell shape and cell condition. Agents that affect cytoskeleton, adhesion, regulatory signaling pathways, cell cycle, cause significant and specific changes in cell morphology.

In drug discovery work, valuable information can be obtained by understanding how a potential therapeutic agent affects a cell. This information may give some indication of the mechanism of action associated with the compound. As present, little or no formal effort has been made to correlate cell condition with cell shape. To the extent that cell shape analyses are performed at all, the results are typically reported in qualitative terms based on observations of cells using various microscopy techniques. Given that there are some known correlations between cell shape and cell condition, the ability to quickly determine whether a population of cells has a particular modified shape could provide a valuable tool in assessing the mechanism of action of an uncharacterized compound that has been tested on the population of cells. Therefore, it would be desirable to have improved techniques for analysis of cell shapes.

SUMMARY OF THE INVENTION

The present invention addresses this need by providing methods and apparatus for the analysis of images of cells and extraction biologically-significant shape-related features from the cell images. The extracted features may be correlated with particular conditions induced by biologically-active agents with which cells have been treated, thereby enabling the automated analysis of cells based on cell shape parameters. In particular, the invention provides methods for segmentation of cells in an image using data from a plurality of separate images of different cell components. One application of the invention involves the use of a reference cell component (preferably one that has been previously segmented and therefore one whose segmentation parameters are well understood and may be repeated) in combination with image data for a second component to perform a segmentation of another cell component or the whole cell. This application of the invention is particularly effective when the reference component has been previously segmented and is present in a single copy in the cell, such as the nucleus, centrosome, specific chromosome, Golgi complex etc. The invention further provides techniques for extraction of biologically-relevant shape-related cell features from segmented cell images.

In accordance with the present invention, image data for a reference cell component, preferably present in the cell in a single copy and/or previously segmented (for example, cell nuclei) are processed together with image data for a cell shape-indicative marker (for example, cytoskeletal components, (e.g., tubulin), one or more cytoplasmic proteins (for example lactate dehydrogenase or total cell protein), or membrane components (e.g., lipids or plasma membrane receptors)) in a watershed technique. Further, the invention provides a skeletonization and skeleton analysis technique for extracting biologically-relevant shape-related features from the segmented images.

One aspect of this invention pertains to a method of identifying boundaries of biological cells. The method involves receiving a first image of a field of one or more cells in which a reference cell component of the one or more cells is identified by a reference cell component marker image parameter, receiving a second image of the field of one or more cells in which at least one of a cell shape-indicative marker of the one or more cells is identified by a cell shape-indicative marker image parameter, and processing the first image in conjunction with the second image so that individual cell boundaries for the one or more cells in the field are identified. The image processing may involve segmenting the one or more reference cell components in the first image to generate a digital representation of the first image, called a reference cell component mask, thresholding the cell shape-indicative marker in the second image to generate a digital representation of the second image including a cell shape-indicative marker portion and a background portion, conceptually registering the nuclei mask with the digital representation of the second image, and applying a watershed algorithm to data provided by the conceptually registered reference component mask and digital representation of the second image such that individual cell boundaries for the one or more cells in the field are identified. In addition, the method may further involve extracting biologically-significant shape-related information from the field of one or more cells.

Another aspect of the invention pertains to a method of extracting biologically-significant shape-related information from a field of one or more cells. The method involves providing a segmented image of the field of one or more segmented cells, where the boundaries of the one or more segmented cells have been ascertained by the segmentation. For each of one or more of the cells in the segmented cell image two endpoints defining two parts of the boundary of the one or more cells are selected. For each part of the cell's boundary, computing the distance from each point on the part of the cell boundary to a line between the endpoints, determining a point $d_{MAX}$ on the portion of the boundary, the point $d_{MAX}$ being maximally distant from the line, and comparing the distance from the point $d_{MAX}$ to a predetermined threshold distance value, $d_{TH}$. Where $d_{MAX}$ is greater than $d_{TH}$, the line between the endpoints is discarded, and point $d_{MAX}$ as a new endpoint together with one of the original endpoints to separate the part into two new parts, and the process from determining a point $d_{MAX}$ is repeated. Where $d_{MAX}$ is less than $d_{TH}$, the line is used as a side of a polygon approximating the cell shape until a polygon approximating the shape of the cell is complete. When the polygon is complete, it is skeletonized, and end points and/or nodes are calculated for the polygon approximation of the cell.

Still another aspect of the invention pertains to a method of correlating a cell's shape with a biological condition of the cell. The method involves providing a plurality of segmented images of fields of one or more segmented cells, where at least one of the fields has been treated with a biologically active agent and at least one of the fields is a control having not been treated with the biologically active agent. The boundaries of the one or more segmented cells having been ascertained by the segmentation. For each of one or more of the cells in the plurality of segmented cell images, two endpoints defining two parts of the boundary of the one or more cells are selected. For each part of the cell's boundary, computing the distance from each point on the part of the cell boundary to a line between the endpoints, determining a point $d_{MAX}$ on the portion of the boundary, the point $d_{MAX}$ being maximally distant from the line, and comparing the distance from the point $d_{MAX}$ to a predetermined threshold distance value, $d_{TH}$. Where $d_{MAX}$ is greater than $d_{TH}$, the line between the endpoints is discarded, and point $d_{MAX}$ as a new endpoint together with one of the original endpoints to separate the part into two new parts, and the process from determining a point $d_{MAX}$ is repeated. Where $d_{MAX}$ is less than $d_{TH}$, the line is used as a side of a polygon approximating the cell shape until a polygon approximating the shape of the cell is complete. When the polygon is complete, it is skeletonized, and end points and/or nodes are calculated for the polygon approximation of the cell. The computations of end points and/or nodes for the polygon approximation of the cell are then computed to identify significant shape differences between the treated and control fields of one or more cells.

Yet another aspect of the present invention pertains to an image analysis apparatus for identifying individual biological cells in a field of cells. The apparatus includes a memory or buffer adapted to store, at least temporarily, a first image of a field of one or more cells, in which a reference cell component of the one or more cells is identified by a reference cell component marker image parameter, and a second image of the field of one or more cells, in which at least one of a cell shape-indicative marker of the one or more cells are identified by a cell shape-indicative marker image parameter. The apparatus further includes a processor configured or designed to process the first image in conjunction with the second image such that individual cell boundaries for the one or more cells in the field are identified.

Another aspect of the invention pertains to a method of identifying boundaries of biological cells. The method involves receiving a first image of the field of one or more cells in which a reference cell component of the one or more cells is identified by a reference cell component marker image parameter, and receiving a second image of the field of one or more cells in which at least one of a cell shape-indicative marker of the one or more cells is identified by a cell shape-indicative marker image parameter. Then, a thresholding techniques is applied the cell shape-indicative marker image parameter in the second image to generate a digital representation of the second image comprising a cell shape-indicative marker portion and a background portion, and the boundaries of individual cells are identified by applying a watershed algorithm to the second image using the reference cell component marker image parameter and the background portion of the digital representation of the second image as seeds.

Another aspect of the invention pertains to computer program products including a machine readable medium on which is stored program instructions for implementing any of the methods described above. Any of the methods of this invention may be represented as program instructions that can be provided on such computer readable media.

These and other features and advantages of the present invention will be described below in more detail with reference to the associated drawings.

DETAILED DESCRIPTION OF THE INVENTION

Introduction

Figure 1:
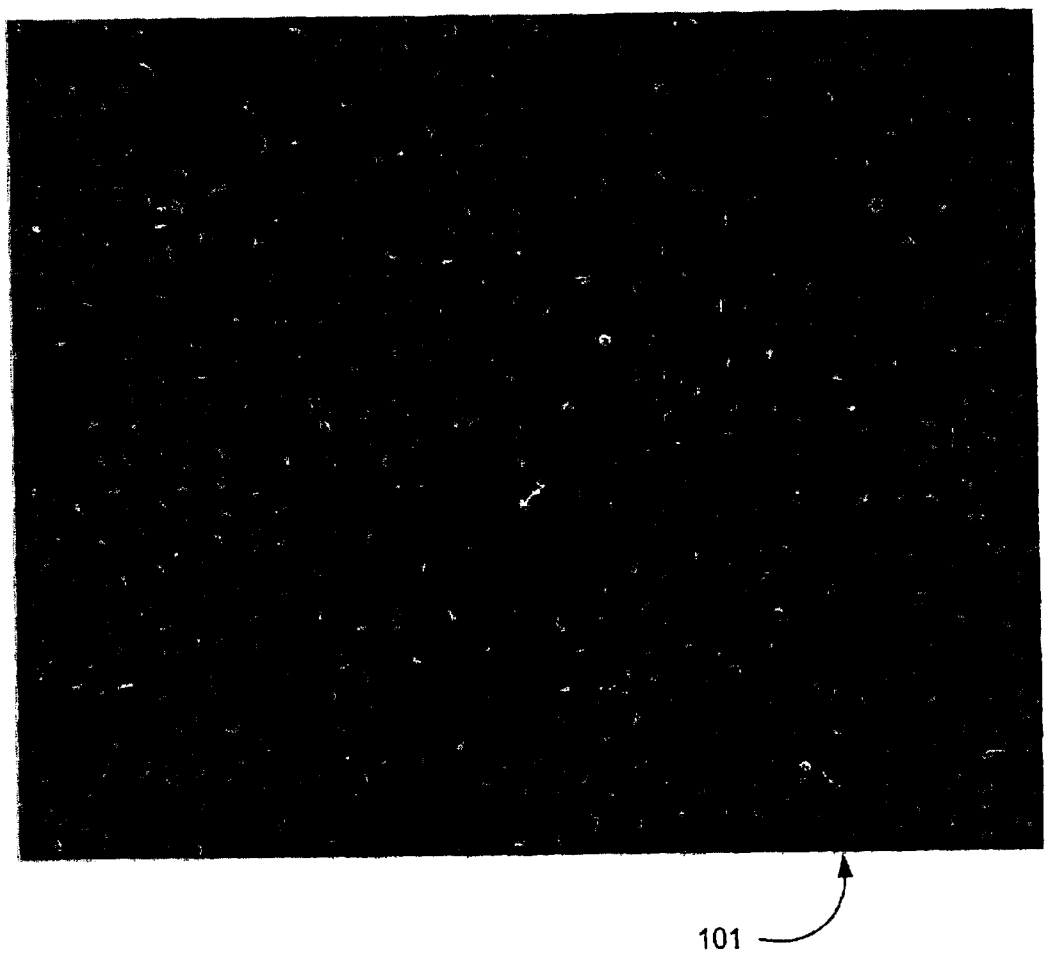
FIG. 1 depicts an image of a field of cells from cell line SF268 that have been treated with rodamine-labeled Dm 1 alpha antibody and imaged so that the extent of the cell shape-indicative cytoskeletal protein tubulin in the field of cells is visible.

Generally, this invention relates to image analysis processes and apparatus configured for image analysis. It also relates to machine-readable media on which is provided instructions, data structures, etc. for performing the processes of this invention. In accordance with this invention, images of cells are manipulated and analyzed in certain ways to extract relevant cell shape-related features. Using those features, the apparatus and processes of this invention, can automatically draw certain conclusions about the biology of a cell.

The invention provides methods and apparatus that for the analysis of images of cells and extraction biologically-significant shape-related features from the cell images. The extracted features may be correlated with particular conditions induced by biologically-active agents (e.g., drugs or drug candidates) with which cells have been treated, thereby enabling the automated analysis of cells based on cell shape parameters. In particular, the invention provides methods for segmentation of cells in an image using data from a plurality of separate images of different cell components. One application of the invention involves the use of a reference cell component (preferably one that has been previously segmented and therefore one whose segmentation parameters are well understood and may be repeated) in combination with image data for a second component to perform a segmentation of another cell component or the whole cell. This application of the invention is particularly effective when the reference component has been previously segmented and is present in a single copy in the cell, such as the nucleus, centrosome, specific chromosome, Golgi complex etc. The invention further provides techniques for extraction of biologically-relevant shape-related cell features from segmented cell images.

In accordance with the present invention, image data for a reference cell component, preferably present in the cell in a single copy and/or previously segmented (for example, cell nuclei) are processed together with image data for a cell shape-indicative marker (for example, cytoskeletal components, (e.g., tubulin), one or more cytoplasmic proteins (for example lactate dehydrogenase or total cell protein), or membrane components (e.g., lipids or plasma membrane receptors)) in a watershed technique. Further, the invention provides a skeletonization and skeleton analysis technique for extracting biologically-relevant shape-related features from the segmented images.

The invention will now be described in terms of particular specific embodiments as depicted in the drawings. However, as will be apparent to those skilled in the art, the present invention may be practiced without the employing some of the specific details disclosed herein. Some operations or features may be dispensed with. And often alternate elements or processes may be substituted. For example, in the following description, nuclei are used as the reference cell component, and tubulin as the cell shape-indicative component to provide image data useful for whole cell segmentation. As noted above, cell components other than nuclei, particularly those previously segmented and/or present in only a single copy in a cell, and other cell shape-indicative components may also be used.

Preparation of the Image

In accordance with the present invention, images may be obtained of cells that have been treated with a chemical agent to render visible (or otherwise detectable in a region of the electromagnetic spectrum) a cellular component. A common example of such agents are colored dyes specific for a particular cellular component that is indicative of cell shape. Other such agents may include fluorescent, phosphorescent or radioactive compounds that bind directly or indirectly (e.g., via antibodies or other intermediate binding agents) to a cell component. In accordance with the present invention, a plurality of cell components may be treated with different agents and imaged separately. For example, in one embodiment, cell nuclei, a previously segmented component present in only a single copy in a cell, and tubulin, a cytoskeletal protein, or other component indicative of cell shape, are treated as described further below.

Generally the images used as the starting point for the methods of this invention are obtained from cells that have been specially treated and/or imaged under conditions that contrast markers of cellular components of interest (e.g., tubulin for the cytoskeleton, and DNA for the nuclei) from other cellular components and the background of the image. In a preferred embodiment, the cells are fixed and then treated with a material that binds to a marker for the components of interest and shows up in an image. Preferably, the chosen imaging agent binds indiscriminately with the marker, regardless of its location in the cell. The agent should provide a strong contrast to other features in a given image. To this end, the agent should be luminescent, radioactive, fluorescent, etc. Various stains and fluorescent compounds may serve this purpose.

A variety of imaging agents are available depending on the particular marker, and agents appropriate for labeling cytoskeletal, cytoplasmic, plasma membrane, nuclear, and other discrete cell components are well known in the histology art. Examples of such compounds include fluorescently labeled antibodies to cytoplasmic or cytoskeletal proteins, fluorescent dyes which bind to proteins and/or lipids, labeled ligands which bind to cell surface receptors, and fluorescent DNA intercalators and fluorescently labeled antibodies to DNA or other nuclear component which bind to the nuclei. For example, a suitable label for the cytoskeletal protein tubulin is a fluorescently labeled monoclonal antibody to tubulin, rodamine-labeled Dm 1 alpha, produced from hybdridoma DM1A reported in the publication Blose et. al. Journal of Cell Biology, V98, 1984, 847–858. Examples of fluorescent DNA intercalators include DAPI and Hoechst 33341 available from Molecular Probes, Inc. of Eugene, Oreg. The antibodies may be fluorescently labeled either directly or indirectly.

In a preferred embodiment, cells may be treated with more than one imaging agent, each imaging agent specific for a different cellular component of interest. The component(s) may then be separately imaged by separately illuminating the cells with an excitation frequency (channel) for the imaging agent of the marker for the component of interest. Thus different images of the same cells focussing on different cellular components may be obtained on different channels.

Various techniques for preparing and imaging appropriately treated cells are described in U.S. patent application Ser. Nos. 09/310,879, 09/311,996, and 09/311,890, previously incorporated by reference. In the case of cells treated with DAPI or other fluorescent material, a collection of such cells is illuminated with light at an excitation frequency. A detector is tuned to collect light at an emission frequency. The collected light is used to generate the image and highlights regions of high marker (e.g., tubulin or DNA) concentration.

In order to derive biologically meaningful cell shape information from an analysis of cell images, it is important to be able to distinguish one cell from another by establishing its boundaries and distinguishing it from other cells in the image (a process sometimes referred to as "segmentation"). FIG. 1 depicts an image 101 of a field of cells from cell line SF268 that have been treated with rodamine-labeled Dm1alpha antibody and imaged at an appropriate wavelength, that is in this case an excitation wavelength for the fluorescent rodamine label on the antibody. In this way, the extent of the cell shape-indicative cytoskeletal protein tubulin in the field of cells is visible. It should be noted that segmentation of cells may be challenging, particularly in an image depicting a crowded field of cells such as depicted in image 101 where cells overlap and/or abut one another. In accordance with one embodiment of the present invention, segmentation is a precursor to extracting features correlated with cell shape that convey useful information about cell shape and condition (a process sometimes referred to as "feature extraction").

Figure 2:
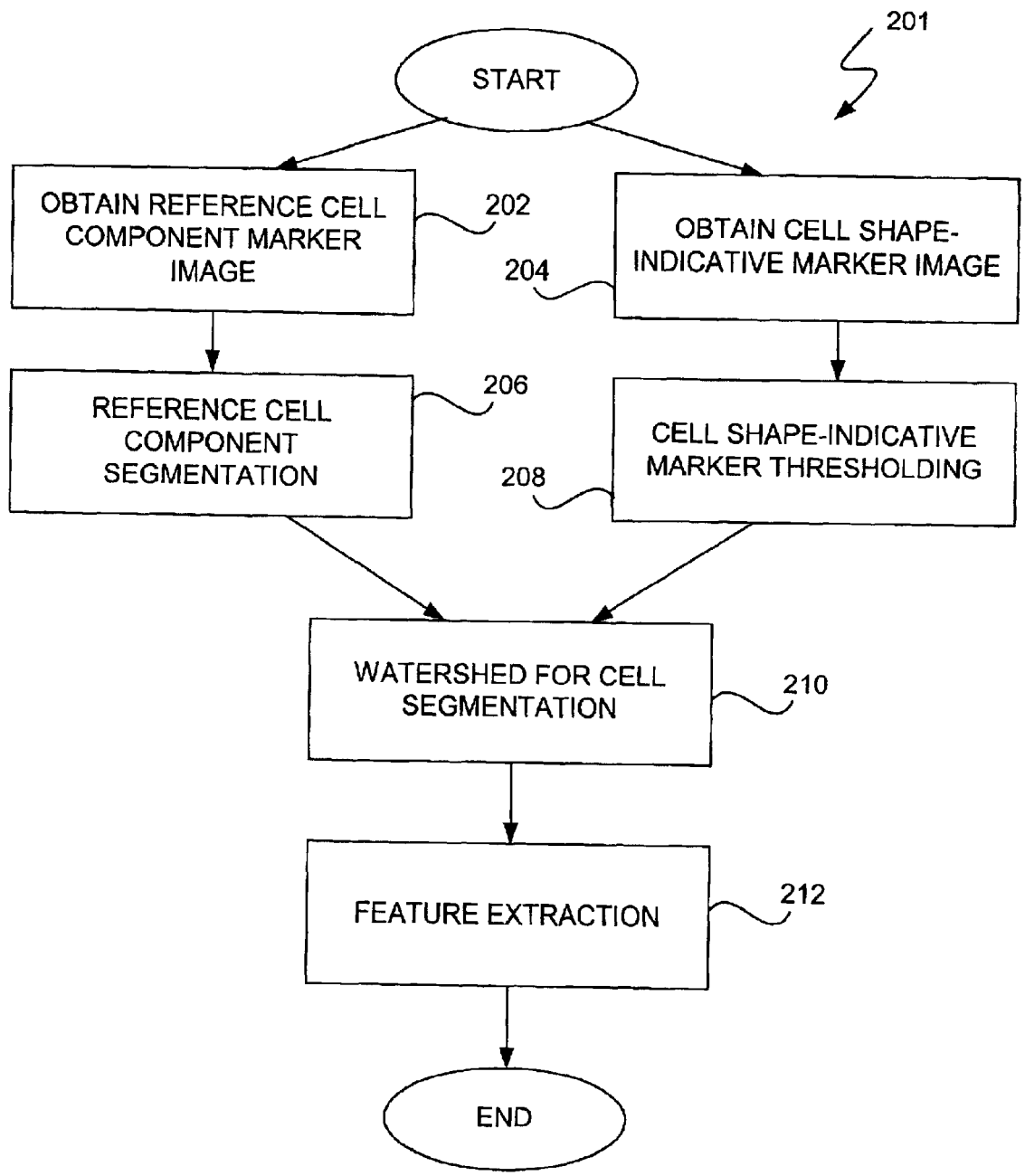
FIG. 2 is a process flow diagram depicting—at a high level—one process of this invention for segmenting an image of cells and analyzing the segmented cell according to its shape-related features.

A high level process flow 201 in accordance with one embodiment of this invention is depicted in FIG. 2. As shown, the process begins at 202, 204 where one or more image analysis tools (typically logic implemented in hardware and/or software) obtain images showing a reference cell component (in this example, cell nuclei; as noted above, images of other cell components, particularly those previously segmented and/or present in a single copy in a cell, may also be used) and one or more cell shape-indicative markers for one or more cells. Typically, images will be taken from an assay plate or other cell support mechanism in which multiple cells are growing or stored. For nuclei, the image is taken in a manner that allows the DNA within the nuclei of the cells to be identified within the image. For a cell shape-indicative marker, an image analysis tool (typically the same tool as used to obtain the nuclei image) obtains an image showing a cell shape-indicative marker in a manner similar to that described above except that the image is taken using a different wavelength (channel) or microscopy technique associated with the cell shape-indicative marker rather than the reference component marker (e.g., DNA for nuclei).

In each case, the image obtained will represent the imaged marker as a corresponding "image parameter." The image parameter will be an intensity value of light or radiation shown in the image. Often, the intensity value will be provided on a per pixel basis. In addition, the intensity value may be provided at a particular wavelength or narrow range of wavelengths that correspond to the emission frequency of an imaging agent that specifically associates with the imaged marker.

In the following discussion and the figures of the present application, the reference cell component and cell shape-indicative marker used to describe and illustrate the principles of the present invention are nuclei and the cytoskeletal protein, tubulin, respectively. However, as noted above, the invention is not limited to the use of nuclei and tubulin as the reference cell component and cell shape-indicative marker. Instead, it should be understood that cell components other than nuclei, particularly those previously segmented and/or present in only a single copy in a cell, may also be used, and that tubulin is just one example of an array of markers that may be correlated with and indicative of cell shape. Other such reference cell components and cell shape-indicative markers may be used in place of or in conjunction with nuclei and tubulin according to the principles of the invention described herein.

The relevant images obtained at 202, 204 are captured by an image acquisition system. In one embodiment, the image acquisition system is directly coupled with the image analysis tool of this invention. Alternatively, the image under consideration may be provided by a remote system unaffiliated with the image acquisition system. For example, the images may be acquired by a remote image analysis tool and stored in a database or other repository until they are ready for use by an image analysis tool of this invention.

Sometimes corrections must be made to the measured intensity. This is because the absolute magnitude of intensity can vary from image to image due to changes in the staining and/or image acquisition procedure and/or apparatus. Specific optical aberrations can be introduced by various image collection components such as lenses, filters, beam splitters, polarizers, etc. Other sources of variability may be introduced by an excitation light source, a broad band light source for optical microscopy, a detector's detection characteristics, etc. Even different areas of the same image may have different characteristics. For example, some optical elements do not provide a "flat field." As a result, pixels near the center of the image have their intensities exaggerated in comparison to pixels at the edges of the image. A correction algorithm may be applied to compensate for this effect. Such algorithms can be easily developed for particular optical systems and parameter sets employed using those imaging systems. One simply needs to know the response of the systems under a given set of acquisition parameters.

Reference Cell Component Segmentation

After the nuclei image has been obtained at 202, the image analysis tool segments the image into discrete nuclei representations at 206. The goal of segmentation is to convert the image into discrete images/representations for the DNA of each nucleus to generate a "nuclei mask" to be used in conjunction with cell shape-indicative marker image data in a cell segmentation process in accordance with the present invention. In a preferred embodiment, each representation includes only those pixels where the DNA of a single cell nucleus is deemed to be present. Since the DNA is normally contained almost entirely within the nucleus of non-mitotic eucaryotic cells, the shape of each representation resulting from segmentation represents the boundaries within which a nucleus lies. The nuclei mask is a composite of the discrete nuclei representations providing intensity as a function of position for each nuclei in the image.

Individual cell nucleus representations may be extracted from the image by various image analysis procedures. Preferred approaches include edge finding routines and thresholding routines. Some edge finding algorithms identify pixels at locations where intensity is varying rapidly. For many applications of interest here, pixels contained within the edges will have a higher intensity than pixels outside the edges. Thresholding algorithms convert all pixels below a particular intensity value to zero intensity in an image subregion (or the entire image, depending upon the specific algorithm). The threshold value is chosen to discriminate between nucleus (DNA) images and background. All pixels with intensity values above threshold in a given neighborhood are deemed to belong to a particular cell nucleus.

Figure 3:
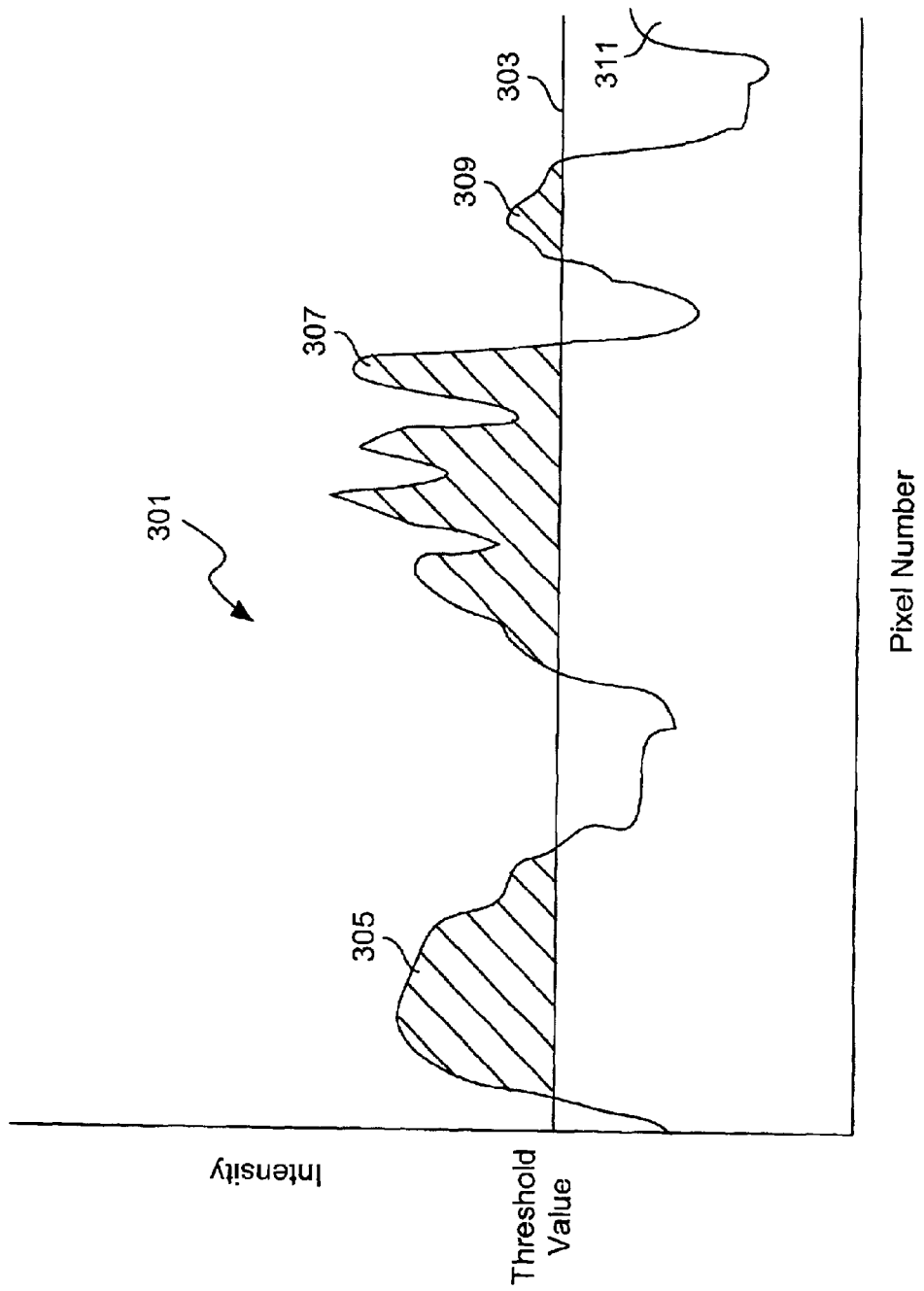
FIG. 3 is a plot of intensity versus pixel location in an image and showing how thresholding may be used to segment an image into individual cells.

The concepts underlying thresholding are well known. The technique is exemplified in FIG. 3, which presents a plot 301 of intensity versus pixel location for an entire image such as image 101. For simplicity, pixels from a single row of an image are considered. A threshold value 303 is chosen to extract those features of the image having intensity values deemed to correspond to actual cell nuclei. In this example, peaks 305, 307, and 309 all contain collections of pixels having intensity values above threshold 303. Therefore, each of these is deemed to be a separate nucleus for extraction during segmentation. Because peak 311 lies entirely below threshold 303, it is not identified as a discrete cell nucleus.

An appropriate threshold may be calculated by various techniques. In a specific embodiment, the threshold value is chosen as the mode (highest value) of a contrast histogram. In this technique, a contrast is computed for every pixel in the image. The contrast may be the intensity difference between a pixel and its neighbors. Next, for each intensity value (0–255 in an eight byte image), the average contrast is computed. The contrast histogram provides average contrast as a function of intensity. The threshold is chosen as the intensity value having the largest contrast. See "The Image Processing Handbook," Third Edition, John C. Russ 1999 CRC Press LLC IEEE Press, and "A Survey of Thresholding Techniques," P. K. Sahoo, S. Soltani and A. K. C. Wong, Computer Vision, Graphics, and Image Processing 41, 233–260 (1988), both of which are incorporated herein by reference for all purposes. In a specific embodiment, edge detection may involve convolving images with the Laplacian of a Guassian filter. The zero-crossings are detected as edge points. The edge points are linked to form closed contours, thereby segmenting the relevant image objects. See The Image Processing Handbook, referenced above. Further details regarding the segmentation of nuclei in accordance with the present invention and associated apparatus and techniques are described in co-pending patent application Ser. Nos. 09/729,754 and 09/792,012 (Publication No. 20020141631, the disclosures of which have been previously incorporated by reference herein.

Cell Shape-Indicative Marker Thresholding

Figure 4A:
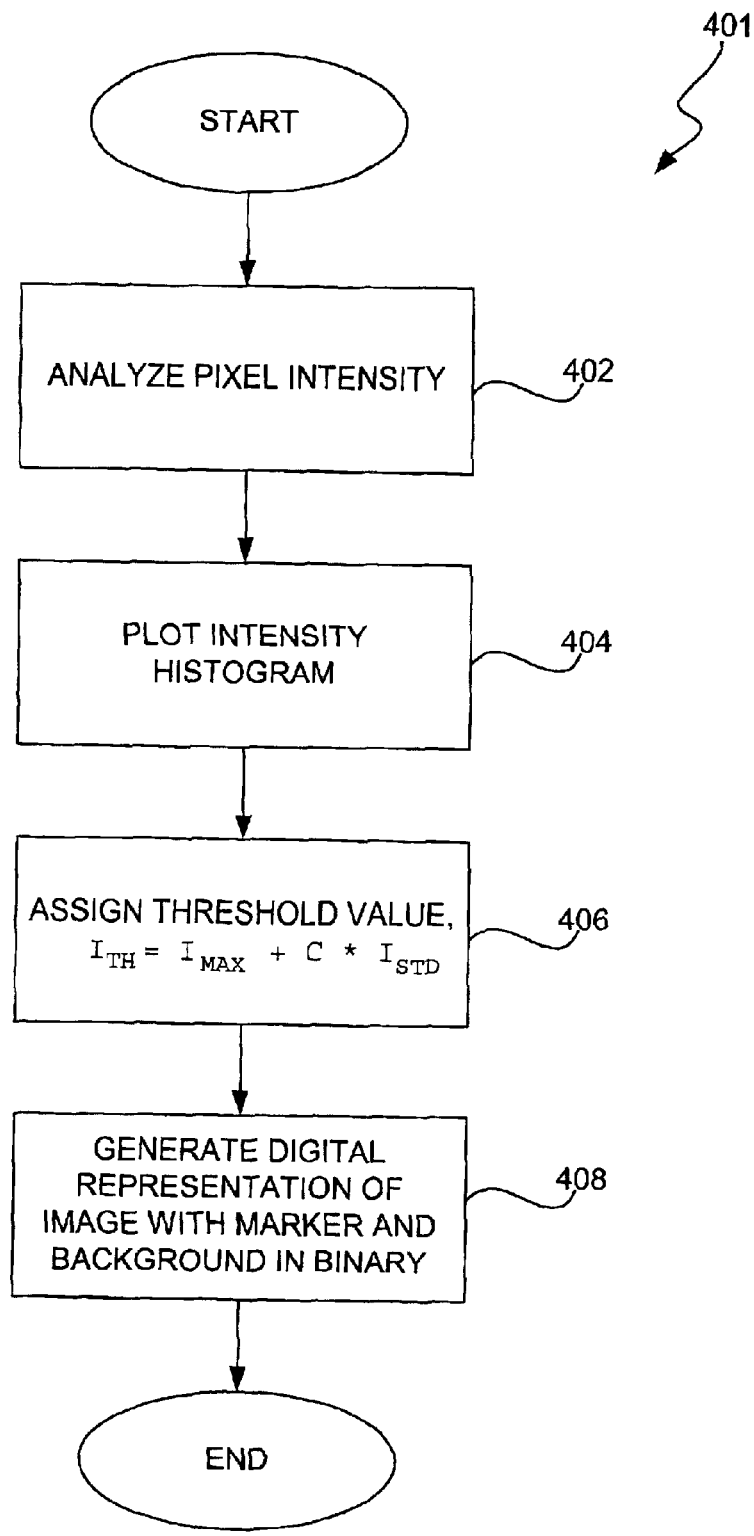
FIG. 4A is a process flow diagram illustrating an image analysis process in accordance with the present invention that produces a preliminary threshold-based cell segmentation.

After the tubulin image has been obtained at 206, the image analysis tool invokes a thresholding algorithm to convert the image to a binary representation of the image. See 208. As noted above, the concepts underlying thresholding in general are well known. However, in a preferred embodiment of the present invention, a particular technique for calculating the tubulin (or other cell shape-indicative marker) threshold is used. In this case, the threshold value is chosen to discriminate between tubulin and background. All pixels with intensity values above a particular (threshold) intensity value zero in an image subregion (or the entire image, depending upon the specific algorithm) are deemed to represent tubulin and are set to a non-zero value. All pixels the threshold value are set to zero and are deemed to represent background. Of course, the values assigned the marker (tubulin) and background are relative and may be reversed so that the marker is non-zero and the background zero. A cell shape-indicative marker thresholding algorithm in accordance with the invention is illustrated in the process flow 401 of FIG. 4A.

Figure 4B:
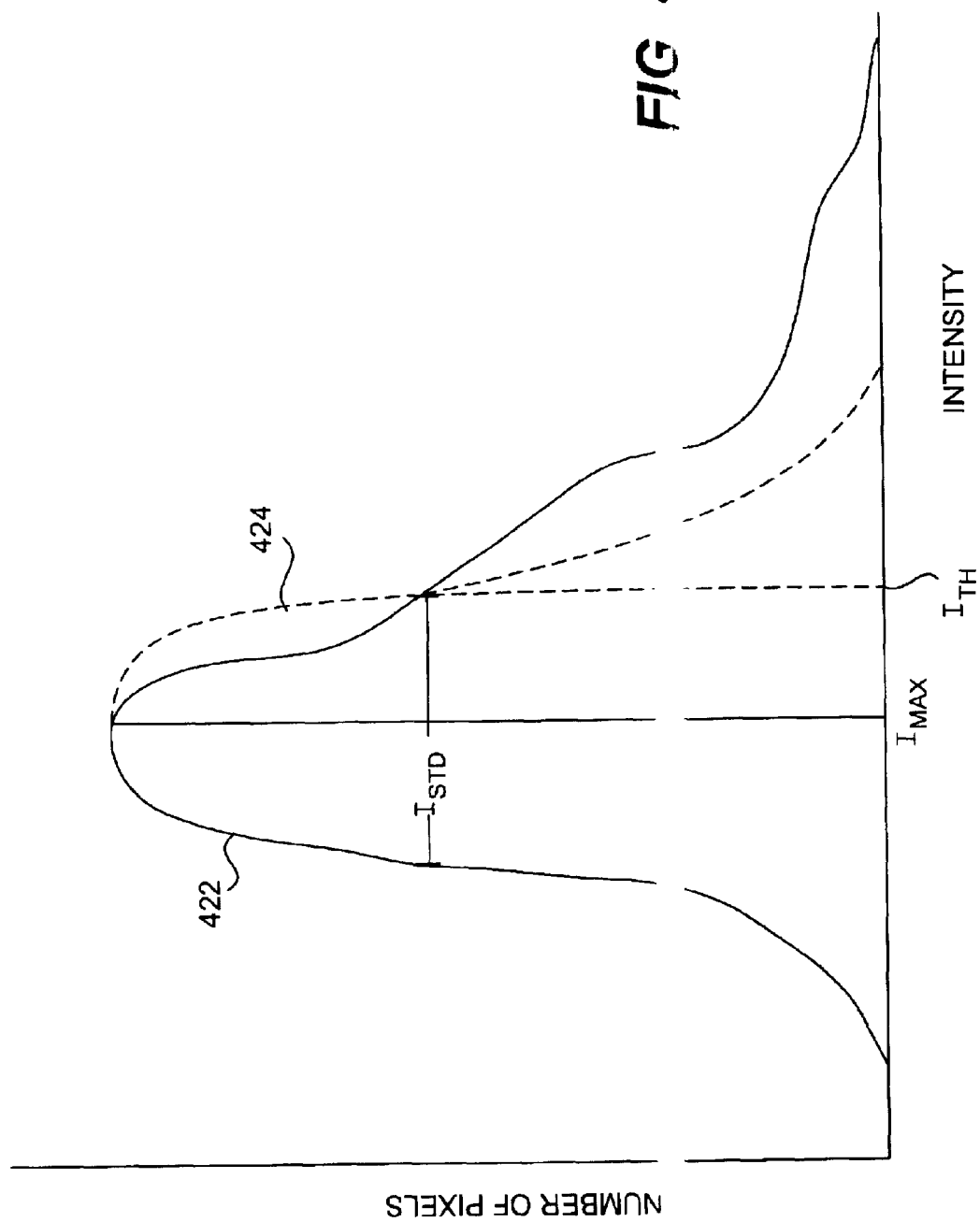
FIG. 4B is an illustration of calculating a threshold value based on an intensity histogram in accordance with the present invention.
Figure 4C:
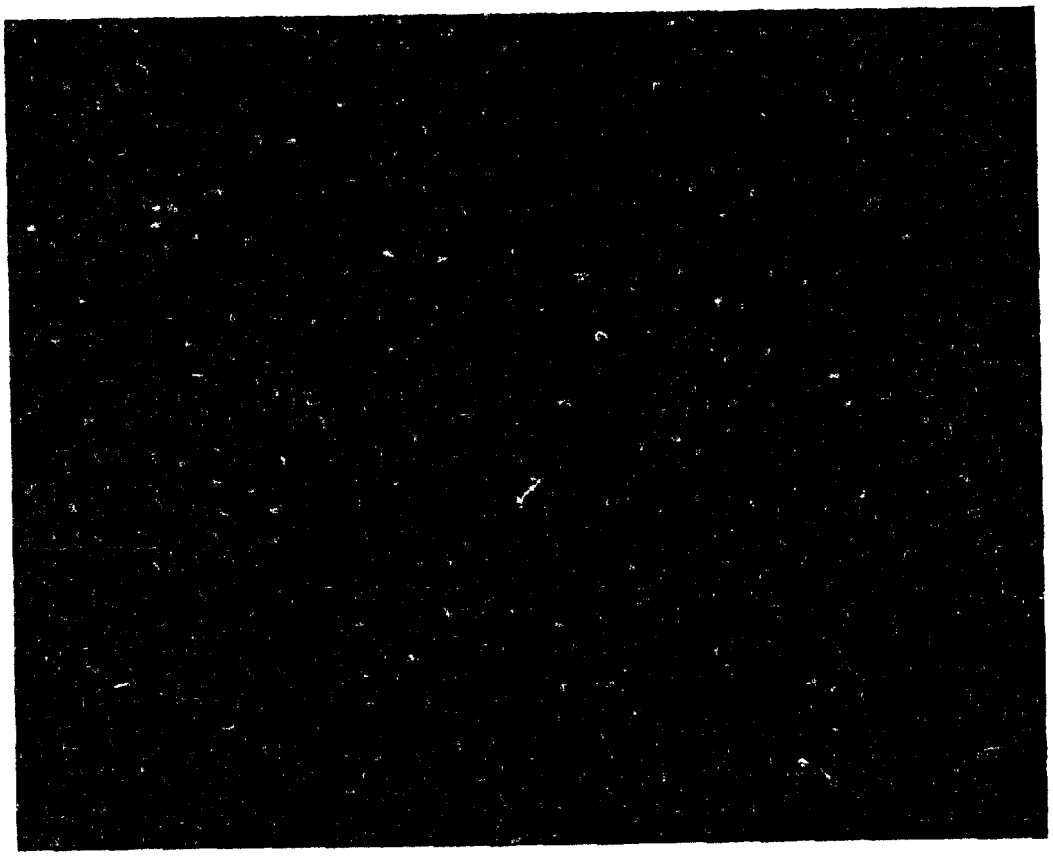
FIG. 4C is a binary image, representing a preliminary threshold-based cell segmentation in accordance with the present invention showing cells stained with antibodies to tubulin overlaid with a rough periphery of objects identified by the thresholding algorithm.

The intensity is then analyzed for every pixel in the image. See 402 A histogram of the number of pixels having a given range of intensities over the range of intensities analyzed is computed. The histogram may be visualized as graphically depicted in FIG. 4B. See 404. The threshold is chosen according to the following function:

$$I_{TH} = I_{MAX} + c \ast I_{STD}$$

where $I_{TH}$ is the threshold, $I_{MAX}$ is the intensity of the greatest number of pixels (assumed to be the background), c is a constant selected on empirical evidence suggesting its suitability for the purpose, and $I_{STD}$ is computed as follows: A symmetrical curve 424 of the left part of the histogram 422 up to the vertical line denoting Imax in FIG. 4B, is computed for the right side of the $I_{MAX}$ line. The combination of the two portions of the curve 422, 424 is fitted by normal distribution. $I_{STD}$ is the standard deviation of this normal distribution. See 406. In a preferred embodiment of the present invention, c is between about 0.7 and 0.9, most preferably, 0.8. Once the threshold value, $I_{TH}$, has been calculated, the image analysis tool makes a determination on a pixel-by-pixel basis of the image to convert the image to a binary digital representation of the image, with the binary elements designating, on the one hand, tubulin, and on the other hand, background (not tubulin). This binary image, representing a preliminary threshold-based cell segmentation, is depicted in FIG. 4C showing cells stained with antibodies to tubulin overlaid with a rough periphery of objects identified by the thresholding algorithm. As described further below, the resulting digital representation is further processed in conjunction with the nuclei mask, discussed above, to achieve an enhanced final segmentation of the cells in the original image.

Application of Watershed Algorithm

Figure 5A:
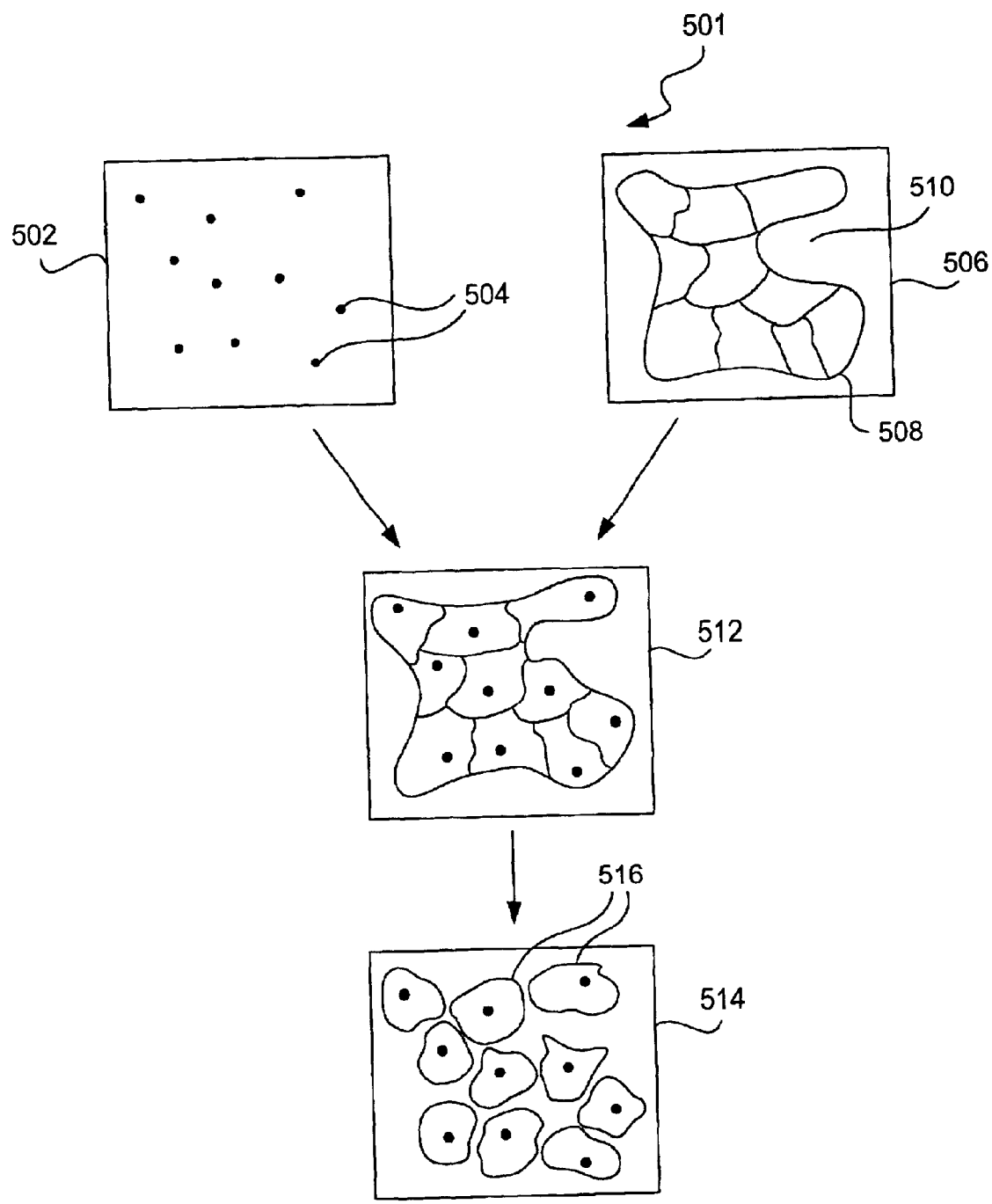
FIG. 5A visually describes steps of a cell segmentation procedure in accordance with the present invention.

Referring now to FIG. 5A, the digital images resulting from the nuclei segmentation, the nuclei mask 502, and the result of tubulin image thresholding, the binary tubulin image 506, are depicted. Each of the digital images has been obtained from a common original field of cells by an image acquisition tool operating in a different channel to obtain each image, as described more fully above. The nuclei mask 502 depicts the nuclei 504 of the cells in the original image. The binary tubulin image 506 depicts an outline of the regions of the original image where tubulin is present 508. The area not contained within the tubulin outline is considered background 510.

Figure 5B:
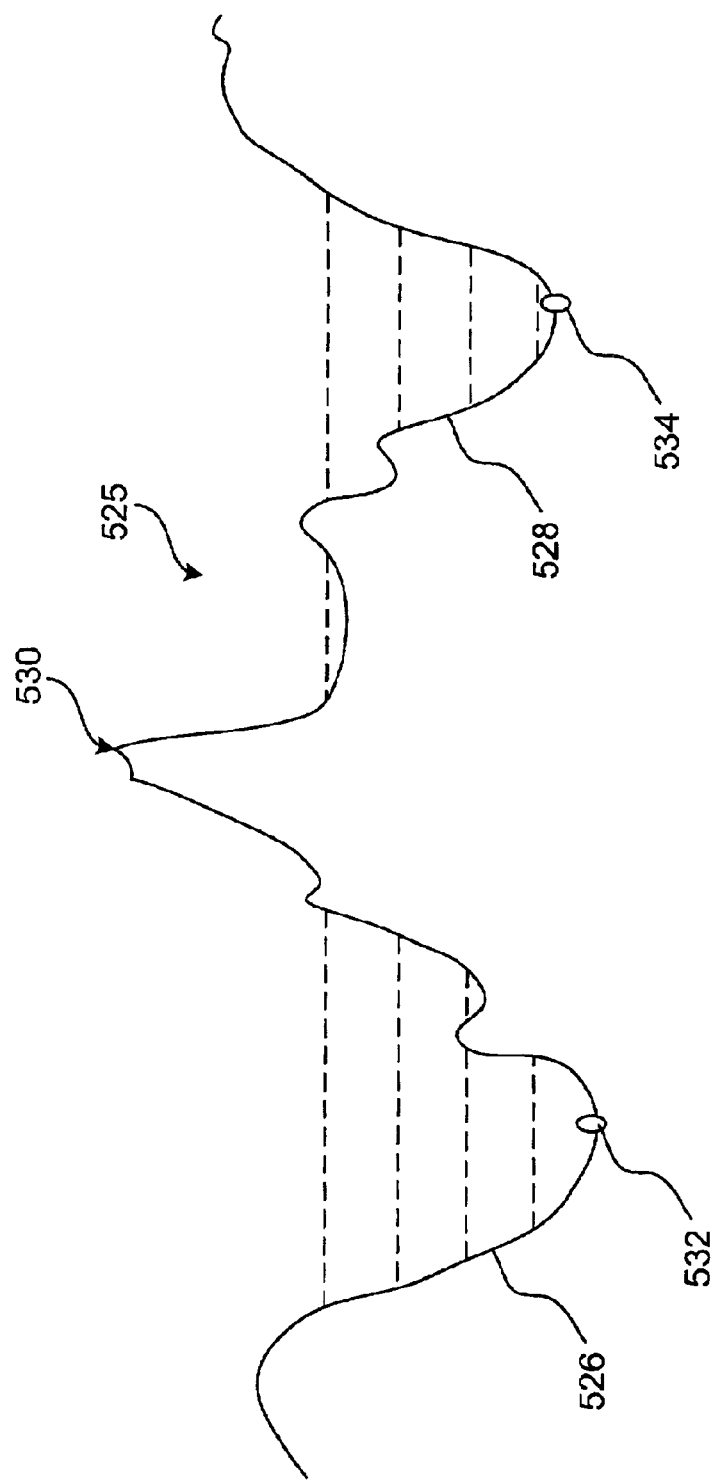
FIG. 5B depicts a visual illustration of a watershed algorithm.

These digital images are now processed in conjunction with each other using a watershed technique in order to achieve segmentation of the cells in the original image. See 210. The concepts underlying watershed algorithms are well known The technique is illustrated by way of a geographic analogy in FIG. 5B, which presents a cross-section of a topology 525. The topology has peaks and valleys of various magnitudes, and includes two particularly deep valleys 526 and 528 containing the low-points of the topology, and a particularly high peak 530 between the valleys 526, 528. The high peak 530 represents the point at which the two valleys 526, 528 ultimately meet, by way of analogy, the point at which bodies of water rising from springs 532 and 534 (referred to as "seeds" in watershed terminology) at the base of the valleys 526, 528 would meet, and thus represents the ultimate boundary of the two valleys 526, 528. top of the high peak is referred to as a "watershed."

The parameters required for application of a watershed algorithm are an image and seeds. According to the present invention, a watershed algorithm is applied to the digital image data contained in the nuclei mask and the digital tubulin (or other cell-shape indicative marker) image in order to elucidate cell boundaries for segmentation of the cells. Referring again to FIG. 5A, nuclei mask 502 and binary tubulin image 506(in particular here, the background of the original tubulin image 510) are conceptually registered to form a composite digital image 512. By conceptually registered it is meant that the spatially corresponding pixels of each of the images are considered together. This composite digital image 512 contains all of the necessary seeds to apply a watershed algorithm on the original tubulin image 204. In this application of watershed, the original tubulin image (101 in FIG. 1) provides a "container component", and the seeds are the nuclei of the nuclei mask and the background of the digital tubulin image. Given these parameters, one of skill in the art can apply known watershed algorithms to the cell image data in order to elucidate watersheds (cell boundaries) and thereby achieve segmentation of the cells in the image. Image 514 (FIG. 5A) represents the segmented image following watershed in which individual cells 516 and, importantly, their shapes, may be seen.

Appropriate watershed algorithms suitable for use in accordance with the present invention are described in detail in L. Vincent and P. Soille, Watersheds in digital spaces: an efficient algorithm based on immersion simulations, IEEE Transactions on Patter Analysis and Machine Intelligence, 13:583–589, 1991, incorporated by reference herein for all purposes.

Figure 5C:
FIG. 5C provides a segmented cell image following application of a watershed algorithm in accordance with the present invention. showing cells stained with antibodies to tubulin, overlaid with a periphery of objects identified by the segmentation algorithm.

FIG. 5C provides a segmented cell image 551 of image 101 (FIG. 1) following application of a watershed algorithm in accordance with the present invention. It should be noted that the boundaries of the cells, and hence the cells' shapes are clearly delineated. The segmented cell image is now well-suited for extraction of shape-based cell features.

Feature Extraction

At some point, an image analysis process must obtain image parameters relevant to a biological condition of interest. Typically, the parameters of interest relate to the size, shape, contour, and/or intensity of the cell images. Examples of some specific parameters for analyzing cell shape include the following:

| | |
|---|---|
| Total Intensity | sum of pixel intensities in an object |
| Average Intensity | average intensities in an object |
| Area | number of pixels in an object |
| Axes Ratio | ratio of lengths of axes of a fitted ellipse |
| Eccentricity | distance from the center of an ellipse to its focus |
| Solidity | measure of pixels inside versus pixels outside an object surrounded by a simple shape |
| Extent | the area of the object divided by area of the smallest box to contain the object. |
| X_coord | the X coordinate of an object's centroid |
| Y_coord | the Y coordinate of object's centroid |
| Form Factor | characteristic of the shape of the outline of an object |
| Diameter | the equivalent diameter of an object, that is the diameter of the circle with the same area as the object |
| Moment | characteristic of the shape of an outline of an object, also taking into account the distribution of pixels inside the object. |

Image analysis routines for extracting these various parameters and others can be designed using well known principles. See The Image Processing Handbook, referenced above. In addition, various commercially available tools provide suitable extraction routines. Examples of some of these products include the MetaMorph Imaging System, provided by Universal Imaging Corporation, a company with headquarters in West Chester, Pa. and NIH Image, provided by Scion Corporation, a company with headquarters in Frederick, Md.

Figure 6A:
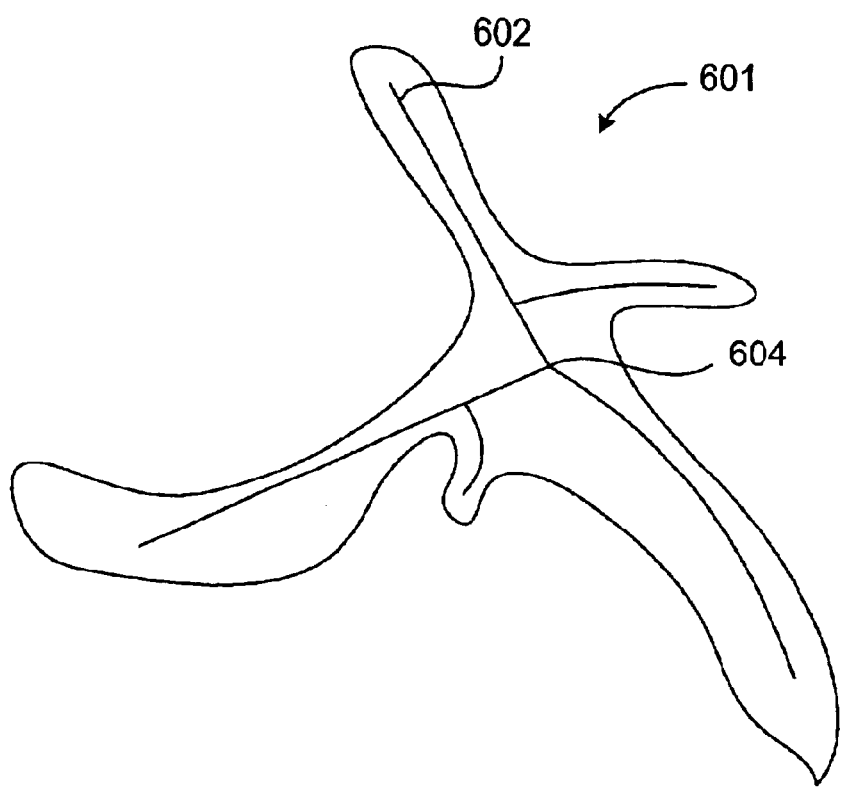
FIG. 6A provides an illustration of a skeleton and skeleton end points and nodes in a cellular context.

The present invention also provides for the extraction of some novel features associated with cell shape and thus may be used to correlate cell shape information with particular cell conditions, for example a condition resulting from the treatment of cells with a putative toxic or therapeutic agent. See 212. The particular features of interest are skeletal end points and nodes of object masks. FIG. 6A provides an illustration of a skeleton and skeleton end points and nodes in the cellular context. The skeleton may be defined by end point 602 and node 604 parameters. An end point 602 is a point at the terminus of a skeleton branch in the cell. Nodes occur at points of intersection of the skeleton represented as lines or curves connecting end points.

Skeletonization techniques, and techniques for the computation of end points and nodes, from an object's skeleton are well known. See, for example, J. C. Russ, The Image Processing Handbook, CRC press, 1998, previously incorporated by reference herein. However, these techniques have not been used to extract features from biological cells because standard skeletonization algorithms have been found to produce poor results biological context. In particular, standard algorithms tend to be more sensitive to branching patterns common along cell membranes that is desirable to produce biologically significant results.

The present invention provides techniques for extracting biologically significant end point and node parameters from images of cells. This is achieved by essentially simplifying the cell shape to a point where the end point and node branching pattern obtained from analysis of the cell image by application of known skeletonization techniques is reduced to a basic level that characterizes the cell in a biologically significant manner. Preferably, this requires that the cell shape be simplified to eliminate "noise" without significant loss of cell shape features that convey information characteristic of the cell condition.

Figure 6B:
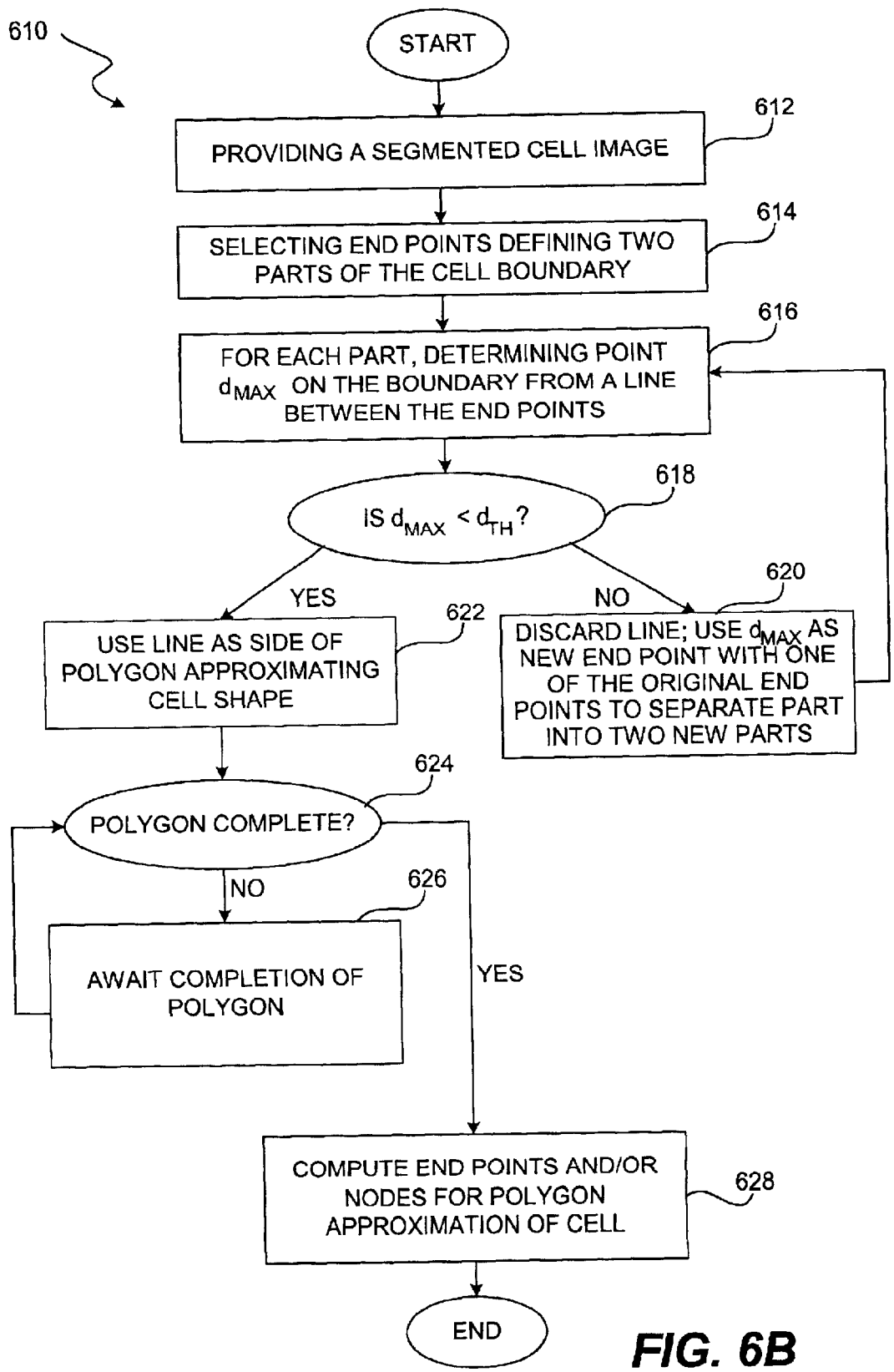
FIG. 6B is a process flow diagram illustrating an image analysis process in accordance with the present invention for generating a polygon that approximates the shape of a cell/object.

In a preferred embodiment, the invention accomplishes this by a process of adjustable polygon cell shape approximation. An algorithm illustrating a preferred embodiment of this process is depicted in the process flow 610 of FIG. 6B. The method of adjustable polygon cell shape approximation begins with an image of a cell whose boundary has been ascertained, typically a segmented cell image from an image depicting multiple cells, such as obtained by the techniques described herein above (612). A pair of points are selected along the boundary of the cell. These points are designated as endpoints (614). These two end points separate the closed cell boundary into two parts. The same procedure is followed iteratively for each of the two parts. For each part, the distance from each point to the line between the endpoints is computed, and a point $d_{MAX}$ on the portion of the cell boundary which is maximally distant from the line, is determined (616).

The distance from the point $d_{MAX}$ to a predetermined threshold distance value, $d_{TH}$, is then compared (618). The threshold distance value, $d_{TH}$, is computed according the following function:

$$d_{TH} = c*A$$

where A is the area of the cell and c is a constant selected on empirical evidence suggesting its suitability for the purpose. In a preferred embodiment of the present invention, c is between about 1/50 and 1/100, most preferably, 1/80.

If $d_{MAX}$ is greater than $d_{TH}$, the line between the endpoints is discarded, point $d_{MAX}$ is used as a new endpoint together with one of the original endpoints, this part of boundary is separated into two new parts and the process for determining $d_{MAX}$ is repeated iteratively for each of the two new parts (620). When $d_{MAX}$ is less than $d_{TH}$, the line between the endpoints is used as a side of a polygon approximating the cell shape (622). The process is repeated until no $d_{MAX}$ is greater than $d_{TH}$ and all the $d_{MAX}$ points selected in this iterative approach and their link lines complete a polygon approximating the shape of the cell (624, 626).

Figure 6C:
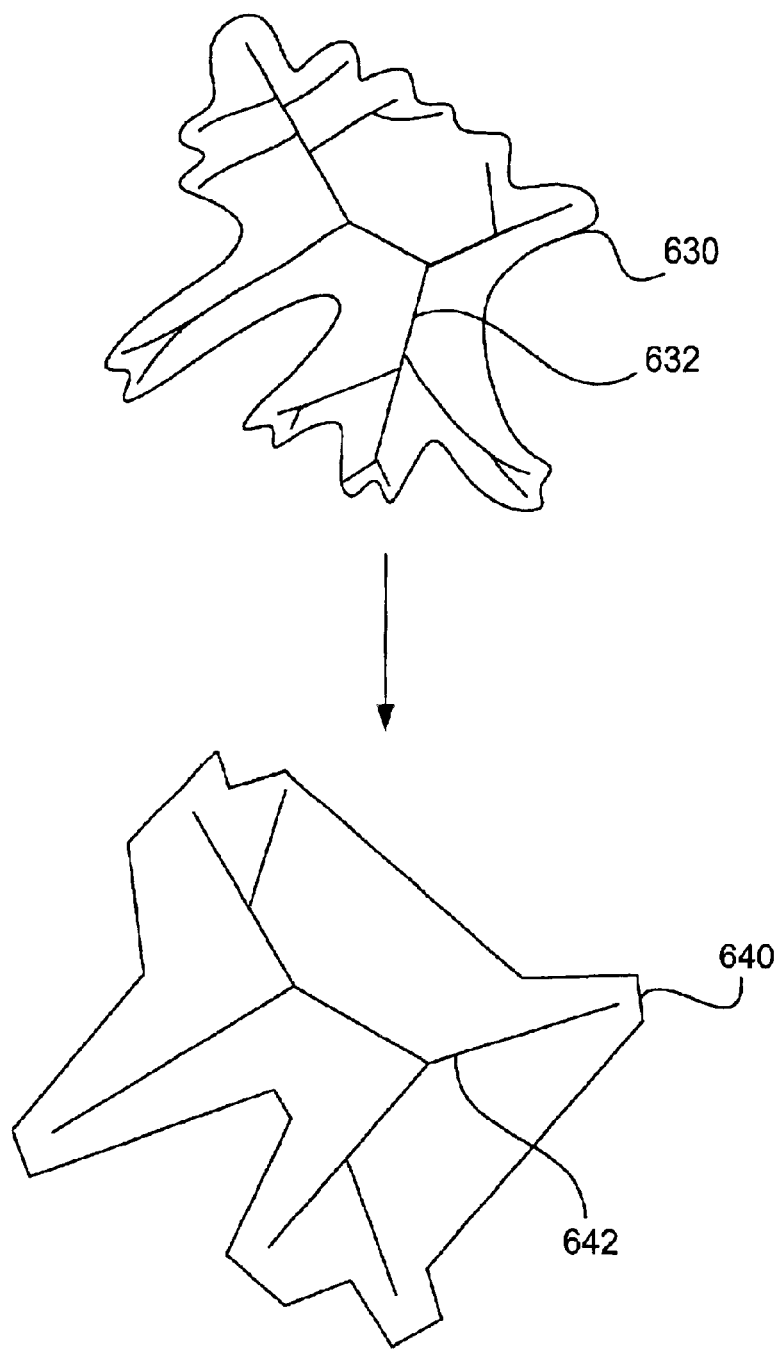
FIG. 6C illustrates an example of how the adjustable polygon cell shape approximation technique of the present invention may be applied to simplify and render biologically significant the end point and node features extracted from a cell following skeletonization.

Upon completion of the polygon approximating the shape of the cell, known skeletonization techniques may be applied to the polygon to generate its skeleton and extract biologically significant end point and node features for the particular cell shape (628). FIG. 6C illustrates an example of how the adjustable polygon cell shape approximation technique of the present invention may be applied to simplify and render biologically significant the end point and node features extracted from a cell following skeletonization. A cell 630 is shown with a complex shape that results in the generation of a complex biologically insignificant skeleton composed of end points and nodes 632 according to conventional skeletonization/branch counting techniques. Below, a polygon 640 approximating the shape of the cell generates a much simpler skeleton 642 with biologically significant end points and nodes. Thus, by permitting the identification and counting of biologically significant end points and/or nodes, the technique provides a way to quantify differences in the condition of cells based on cell shape parameters.

Software/Hardware

Generally, embodiments of the present invention employ various processes involving data stored in or transferred through one or more computer systems. Embodiments of the present invention also relate to an apparatus for performing these operations. This apparatus may be specially constructed for the required purposes, or it may be a general-purpose computer selectively activated or reconfigured by a computer program and/or data structure stored in the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines will appear from the description given below.

In addition, embodiments of the present invention relate to computer readable media or computer program products that include program instructions and/or data (including data structures) for performing various computer-implemented operations. Examples of computer-readable media include, but are not limited to, magnetic media such as hard disks, floppy disks, and magnetic tape; optical media such as CD-ROM disks; magneto-optical media; semiconductor memory devices, and hardware devices that are specially configured to store and perform program instructions, such as read-only memory devices (ROM) and random access memory (RAM). The data and program instructions of this invention may also be embodied on a carrier wave or other transport medium. Examples of program instructions include both machine code, such as produced by a compiler, and files containing higher level code that may be executed by the computer using an interpreter.

Figure 7:
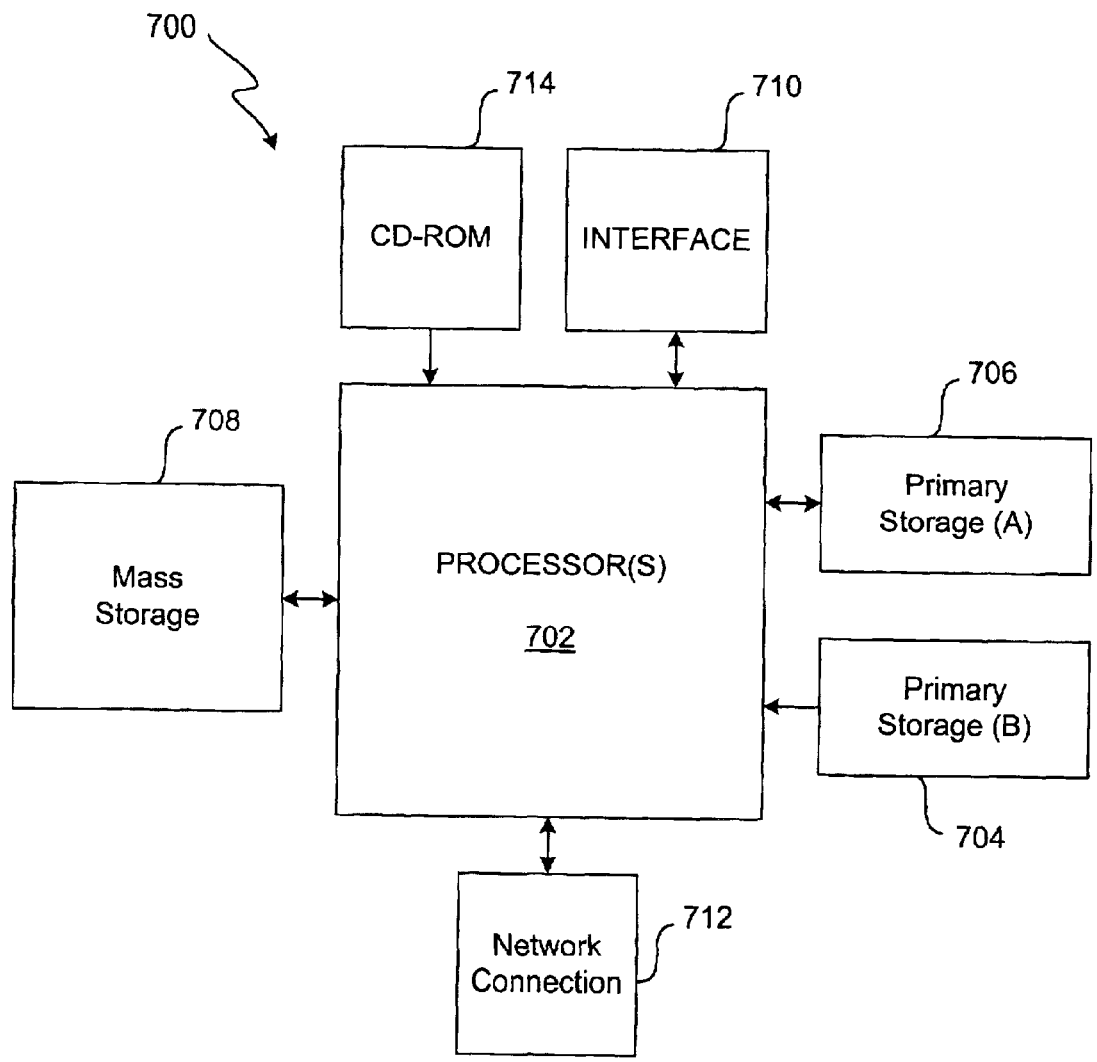
FIG. 7 illustrates a typical computer system that, when appropriately configured or designed, can serve as an image analysis apparatus of this invention.

FIG. 7 illustrates a typical computer system that, when appropriately configured or designed, can serve as an image analysis apparatus of this invention. The computer system 700 includes any number of processors 702 (also referred to as central processing units, or CPUs) that are coupled to storage devices including primary storage 706 (typically a random access memory, or RAM), primary storage 704 (typically a read only memory, or ROM). CPU 702 may be of various types including microcontrollers and microprocessors such as programmable devices (e.g., CPLDs and FPGAs) and unprogrammable devices such as gate array ASICs or general purpose microprocessors. As is well known in the art, primary storage 704 acts to transfer data and instructions uni-directionally to the CPU and primary storage 706 is used typically to transfer data and instructions in a bi-directional manner. Both of these primary storage devices may include any suitable computer-readable media such as those described above. A mass storage device 708 is also coupled bi-directionally to CPU 702 and provides additional data storage capacity and may include any of the computer-readable media described above. Mass storage device 708 may be used to store programs, data and the like and is typically a secondary storage medium such as a hard disk. It will be appreciated that the information retained within the mass storage device 708, may, in appropriate cases, be incorporated in standard fashion as part of primary storage 706 as virtual memory. A specific mass storage device such as a CD-ROM 714 may also pass data uni-directionally to the CPU.

CPU 702 is also coupled to an interface 710 that connects to one or more input/output devices such as such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 702 optionally may be coupled to an external device such as a database or a computer or telecommunications network using an external connection as shown generally at 712. With such a connection, it is contemplated that the CPU might receive information from the network, or might output information to the network in the course of performing the method steps described herein.

In one embodiment, the computer system 700 is directly coupled to an image acquisition system such as an optical imaging system that captures images of cells. Digital images from the image generating system are provided via interface 712 for image analysis by system 700. Alternatively, the images processed by system 700 are provided from an image storage source such as a database or other repository of cell images. Again, the images are provided via interface 712. Once in the image analysis apparatus 700, a memory device such as primary storage 706 or mass storage 708 buffers or stores, at least temporarily, digital images of the cell. Typically, the cell images will show locations where a cell component marker of interest (e.g., DNA, tubulin, etc.) exists within the cells. In these images, local values of a marker image parameter (e.g., radiation intensity) correspond to amounts of the marker at the locations within the cell shown on the image. With this data, the image analysis apparatus 700 can perform various image analysis operations such as distinguishing between individual cells in an image of multiple cells and deciphering cell shape. To this end, the processor may perform various operations on the stored digital image. For example, it may obtain and process multiple images of the same original image using to different channels (e.g., excitation/detection wavelengths) to analyze the image in manner that extracts values of one or more cell shape-indicative parameters that correspond to a cellular condition.

EXAMPLE

The following example provides the results of an experiment showing the effectiveness of techniques in accordance with the present invention for cell segmentation and the extraction of cell features evidencing differences in cell condition. It should be understood the following is representative only, and that the invention is not limited by the detail set forth in this example.

Two fields of HUVEC cells were stained for nuclei with DAPI and for tubulin with rodamine-labeled Dm1alpha antibody, as described above. One of the fields was treated with the anti-actin drug Cytochalasin D in a solution in DMSO. The second field was untreated with any drug, and had only DMSO applied to act as a control. Each field was imaged for nuclei and tubulin and the image data obtained was processed using the thresholding and watershed techniques described above to segment the HUVEC cells in each field. End point features were then extracted from the segmented HUVEC cells in each field using the processes of adjustable polygon cell shape approximation, skeletonization and feature extraction described above.

Figure 8:
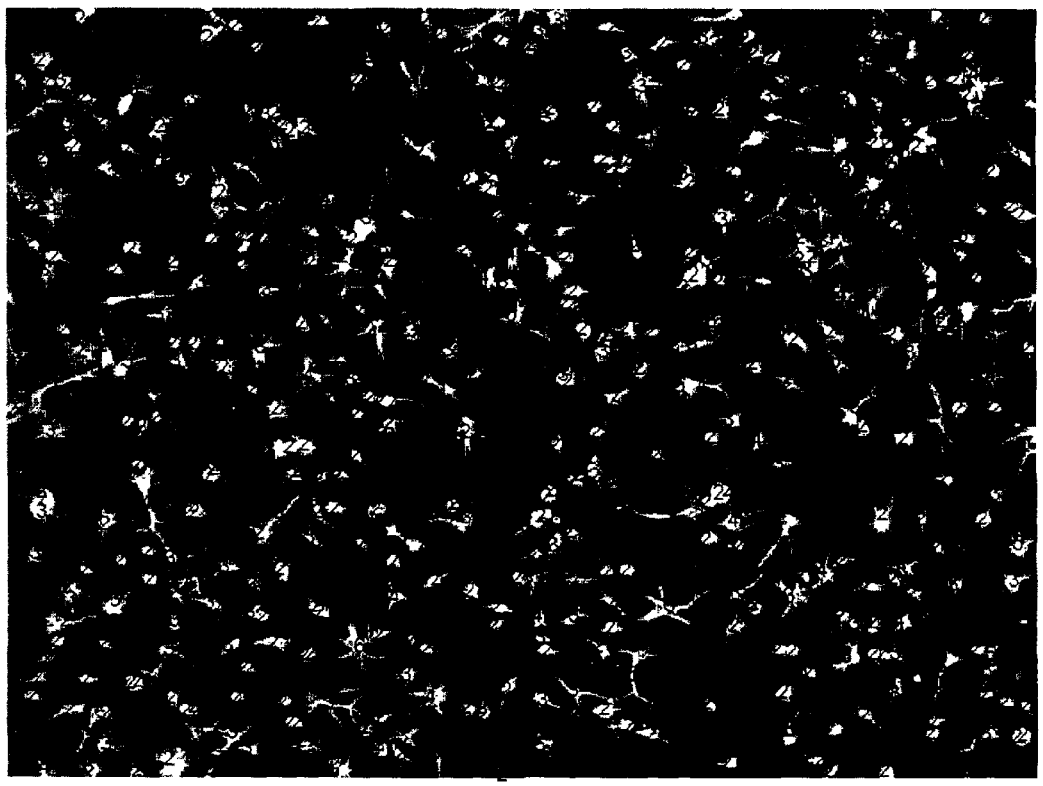
FIGS. 8 and 9 depict the results of an experiment showing the effectiveness of techniques in accordance with the present invention for cell segmentation and the extraction of cell features evidencing differences in cell condition for cells treated with a drug and untreated cells.
Figure 9:
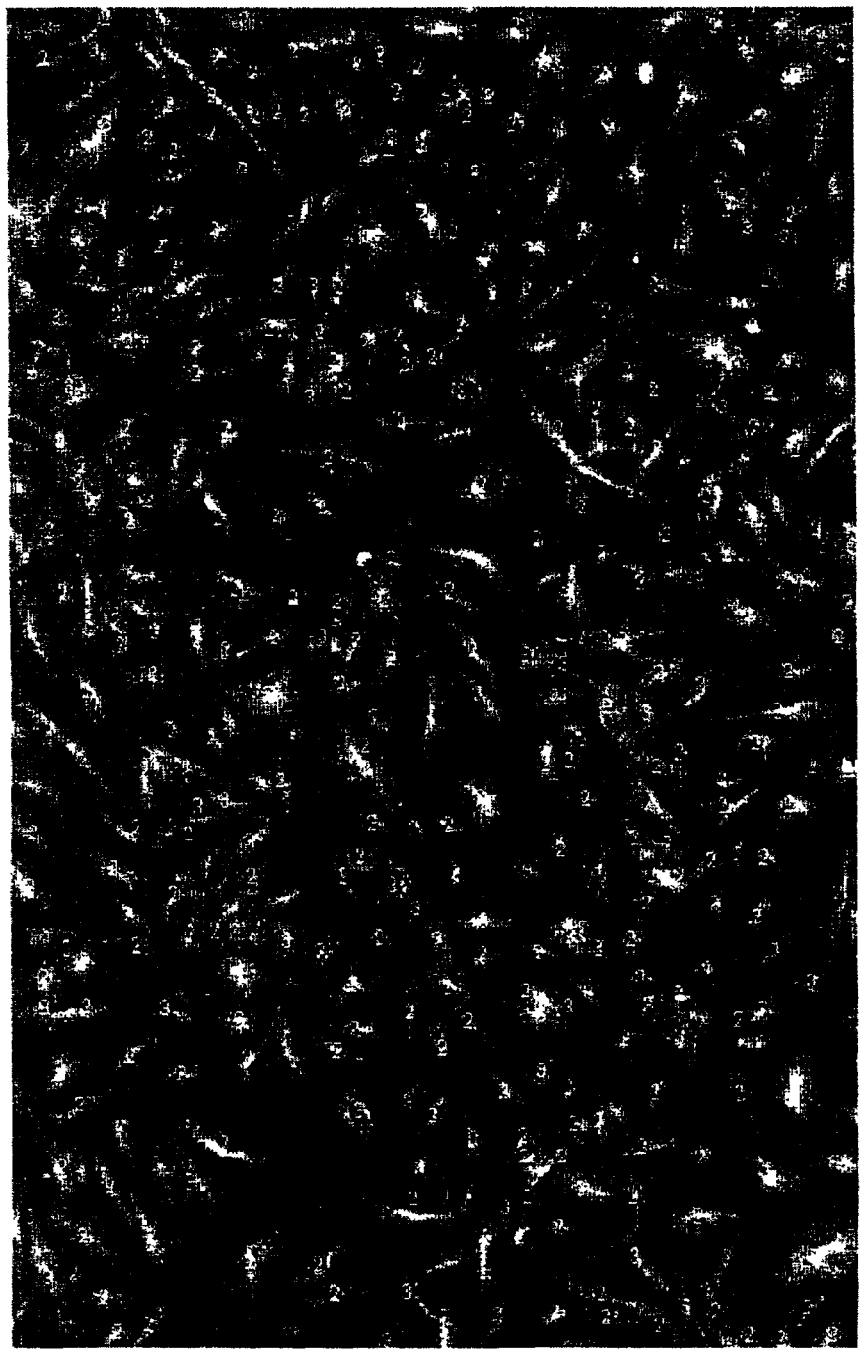

The results are depicted in FIGS. 8 and 9. The numbers on top of the cells represent the number of detected end points of each cell's skeleton. FIG. 8 depicts the image of the field cells treated with anti-actin Cytochalasin D. FIG. 9 depicts the image of the control field of cells to which no drug had been applied. While virtually all of the cells in the control field (FIG. 9) show only 2 end points, a significantly larger proportion of the cells in the drug treated field show an increase in the number of end points (3, 4, 5 and even 6) which reflects an increase in the number of branched (or "arborized" cells). This increase in the number of endpoints in treated relative to the untreated (control) cells may be correlated with the more highly arborized cell condition (phenotype) resulting from treatment of HUVEC cells with anti-actin Cytochalasin D.

Conclusion

Although the foregoing invention has been described in some detail for purposes of clarity of understanding, those skilled in the art will appreciate that various adaptations and modifications of the just-described preferred embodiments can be configured without departing from the scope and spirit of the invention. For example, a variety of reference components and cell shape-indicative markers other than nuclei and tubulin may be used, and the cell segmentation and feature extraction techniques described may be used alone or in combination. Therefore, the described embodiments should be taken as illustrative and not restrictive, and the invention should not be limited to the details given herein but should be defined by the following claims and their full scope of equivalents.

What is claimed is:

1. A method of identifying boundaries of biological cells, the method comprising:

receiving a first image of a field of one or more cells in which a reference cell component of the one or more cells is identified by a reference cell component marker image parameter;

receiving a second image of the field of one or more cells in which at least one cell shape-indicative marker of the one or more cells is identified by a cell shape-indicative marker image parameter;

segmenting the reference cell component in the first image to generate a reference cell component mask of the first image;

thresholding the cell shape-indicative marker in the second image to generate a digital representation of the second image comprising a cell shaped-indicative marker portion and a background portion;

conceptually registering the reference cell component mask with the digital representation of the second image;

applying a watershed algorithm to data provided by the registered reference cell component mask and digital representation of the second image such that idividual cell boundaries for the one or more cells in the field are identified (segmented cells); and extracting biologically-significant features comprising cell skeletal nodes and end points from the one or more segmented cells, the extraction following a skeletonization of the one or more segmented cells, the skeletonization comprising conducting an adjustable polygon shape approximation of the one or more segmented cells, wherein said adjustable polygon cell shape approximation comprises:

(a) providing an image of the one or more segmented cells, the boundary of said one or more segmented cells having been ascertained by the segmentation; for each of one or more of the cells in the segmented cell image, (b) selecting two endpoints defining two parts of the boundary of at least one of said one or more cells;

(c) for each part of said cell boundary, computing the distance from each point on the part of the cell boundary to a line between said endpoints;

(d) determining a point $d_{MAX}$ on the portion of the boundary, said point $d_{MAX}$ being maximally distant from the line;

(e) comparing the distance from the point $d_{MAX}$ to a predetermined threshold distance value, $d_{TH}$;

(f) where $d_{MAX}$ is greater than $d_{TH}$, discarding the line between the endpoints, using point $d_{MAX}$ as a new endpoint together with one of the original endpoints to separate the part into two new parts, and repeating (c) and following; and (g) where $d_{MAX}$ is less than $d_{TH}$, using the line as a side of a polygon approximating the cell shape until a polygon approximating the shape of the cell is complete.

2. The method of claim 1, wherein $d_{TH}=c*A$, where A is the area of the cell and c is a constant.

3. The method of claim 2, wherein $1/50 > c > 1/100$.

4. The method of claim 3, wherein $c=1/80$.

5. A method of extracting biologically-significant shape-related information from a field of one or more cells, comprising:

(a) providing a segmented image of the field of one or more cells, the boundaries of said one or more cells in the image having been ascertained by a method of identifying boundaries of biological cells, the method comprising:

receiving a first image of a field of one or more cells in which a reference cell component of the one or more cells is identified by a reference cell component marker image parameter, receiving a second image of the field of one or more cells in which at least one cell shape-indicative marker of the one or more cells is identified by a cell shape-indicative marker image parameter, and processing the first image in conjunction with the second image such that individual cell boundaries for the one or more cells in the field are identified, whereby the one or more cells of the image are segmented;

for each of one or more of the cells in the segmented cell image, (b) selecting two endpoints defining two parts of the boundary of at least one of said one or more cells;

(c) for each part of said cell boundary, computing the distance from each point on the part of the cell boundary to a line between said endpoints;

(d) determining a point $d_{MAX}$ on the portion of the boundary, said point $d_{MAX}$ being maximally distant from the line;

(e) comparing the distance from the point $d_{MAX}$ to a predetermined threshold distance value, $d_{TH}$;

(f) where $d_{MAX}$ is greater than $d_{TH}$, discarding the line between the endpoints, using point $d_{MAX}$ as a new endpoint together with one of the original endpoints to separate the part into two new parts, and repeating (c) and following;

(g) where $d_{MAX}$ is less than $d_{TH}$, using the line as a side of a polygon approximating the cell shape until a polygon approximating the shape of the cell is complete; and (h) skeletonizing and computing at least one of end points and nodes for the polygon approximation of the cell.

6. The method of claim 5, wherein $d_{TH}=c*A$, where A is the area of the cell and c is a constant.

7. The method of claim 6, wherein $\frac{1}{50}>c>\frac{1}{100}$.

8. The method of claim 7, wherein $c=\frac{1}{80}$.

9. The method of claim 1, wherein said reference cells component is nucleus and said cell shape-inddicative marker is tubulin.

10. A method of correlating a cell's shape with a biological condition of the cell, comprising:

(a) providing a plurality of segmented images of fields of one or more cells, at least one of said fields having been treated with a biologically active agent and at least one of said fields being a control and having not been treated with the biologically active agent, the boundaries of said one or more cells in the images having been ascertained by a method of identifying boundaries of biological cells, the method comprising:

recieving a first image of a field of one or more cells in which a reference cell component of the one or more cells is identified by a reference cell component marker image parameter, receiving a second image of the field of one or more cells in which at least one of a cell shape-indicative marker of the one or more cells is identified by a cell shape-indicative marker image parameter, and processing the first image in conjunction with the second image such that individual cell boundaries for the one or more cells in the field are identified, whereby the one or more cells of the images are segmented;

for each of one or more of the cells in the plurality of segmented cell images, (b) selecting two endpoints defining two parts of the boundary of said cell;

(c) for each part of said cell boundary, computing the distance from each point on the part of the cell boundary to a line between said endpoints;

(d) determining a point $d_{MAX}$ on the portion of the boundary, said point $d_{MAX}$ being maximally distant from the line;

(e) comparing the distance from the point $d_{MAX}$ to a predetermined threshold distance value, $d_{TH}$;

(f) where $d_{MAX}$ is greater than $d_{TH}$, discarding the line between the endpoints, using point $d_{MAX}$ as a new endpoint together with one of the original endpoints to separate the part into two new parts, and repeating (c) and following;

(g) where $d_{MAX}$ is less than $d_{TH}$, using the line as a side of a polygon approximating the cell shape until a polygon approximating the shape of the cell is complete;

(h) skeletonizing and computing at least one of end points and nodes for the polygon approximation of the cell; and (i) comparing the computations of the at least one of end points and nodes for the polygon approximation of the cell to identify significant shape differences between the treated and control fields of one or more cells.

11. The method of claim 10, wherein said computing of at least one of end points and nodes for the polygon approximation of the cell comprises quantifying the at least one of end points and nodes for the polygon approximation of the cell.

12. A computer program product comprising a machine readable medium on which is provided program instructions for identifying individual biological cells in a field of cells, the instructions comprising:

code for receiving a plurality of images of a field of one or more cells, each of the cells comprising a reference cell component and a cell shape-indicative marker, the code for receiving a plurality of images of a field of one or more cells further comprises, code for receiving a first image of said plurality of images of the field of one or more cells in which the reference cell component of the one or more cells is identified by a reference cell component marker image parameter, and code for receiving a second image of said plurality of images of the field of one or more cells in which the cell shape-indicative marker of the one or more cells is identified by a cell shape-indicative marker image parameter; and code for processing the first image in conjunction with the second image such that individual cell boundaries for the one or more cells in the field are identified using the reference cell component marker image parameter and the cell shape-indicative marker image parameter to determine the boundaries of each of the cells or a nonspecific subset of the cells;

wherein said code for processing comprises:

code for segmenting the one or more reference cell components in the first image to generate a reference cell component mask of the first image;

code for thresholding the cell shape-indicative marker in the second image to generate a digital representation of the second image comprising a cell shape-indicative marker portion and a background portion;

code for conceptually registering the reference cell component mask with the digital representation of the second image; and code for applying a watershed algorithm to data provided by the registered reference cell component mask and digital representation of the second image such that individual cell boundaries for the one or more cells in the field are identified(segmented cells); and code for extracting biologically-significant features comprising cell skeletal nodes and end points from the one or more segmented cells, the extraction following a skeletonization of the one or more segmented cells, the skeletonization comprising conducting an adjustable polygon shape approximation of the one or more segmented cells, wherein said adjustble polygon cell shape approximation comprises:

(a) code for providing an image of the one or more segmented cells, the boundary of said one or more segmented cells having been ascertained by the segmentation;

for each of one or more of the cells in the segmented cell image, (b) code for selecting two endpoints defining two parts of the boundary of said cell;

(c) for each part of said cell boundary, code for computing the distance from each point on the part of the cell boundary to a line between said endpoints;

(d) code for determining a point $d_{MAX}$ on the portion of the boundary, said point $d_{MAX}$ being maximally distant from the line;

(e) code for comparing the distance from the point $d_{MAX}$ to a predetermined threshold distance value, $d_{TH}$;

(f) where $d_{MAX}$ is greater than $d_{TH}$, code for discarding the line between the endpoints, code for using point $d_{MAX}$ as a new endpoint together with one of the original endpoints to separate the part into two new parts, and code for repeating (c) and following; and (g) where $d_{MAX}$ is less than $d_{TH}$, code for using the line as a side of a polygon approximating the cell shape until a polygon approximating the shape of the cell is complete.

13. The computer program product of claim 12, wherein $d_{TH}=c^*A$, where A is the area of the cell and c is a constant.

14. The computer program product of claim 13, wherein 1/50>c>1/100.

15. The computer program product of claim 14, wherein c=1/80.

16. A computer program product comprising a machine readable medium on which is provided program instructions for extracting biologically-significant shape-related information from a field of one or more cells, the instructions comprising:

(a) code for providing a segmented image of the field of one or more cells, comprising:
  code for receiving a first image of a field of one or more cells in which a reference cell component of the one or more cell is identified by a reference cell component marker image parameter,
  code for receiving a second image of the field of one or more cells in which at least one cell shape-indicative marker of one or more cells is identified by a cell shape-indicative marker image parameter, and
  code for processing the first image in conjunction with the second image such that indivdual cell boundaries for one or more cells in the field are identified;

for each or one or more cells in the segmented cell image, (b) code for selecting two endpoints defining two parts of the boundary of said cell;

(c) for each part of said cell boundary, code for computing the distance from each point on the part of the cell boundary to a line between said endpoints;

(d) code for determining a point $d_{MAX}$ on the portion of the boundary, said point $d_{MAX}$ being maximally distant from the line;

(e) code for comparing the distance from the point $d_{MAX}$ to a predetermined threshold distance value, $d_{TH}$;

(f) where $d_{MAX}$ is greater than $d_{TH}$, code for discarding the line between the endpoints, code for using point $d_{MAX}$ as a new endpoint together with one of the original endpoints to separate the part into two new parts, and code for repeating (c) and following;

(g) where $d_{MAX}$ is less than $d_{TH}$, code for using the line as a side of a polygon approximating the cell shape until a polygon approximating the shape of the cell is complete; and (h) code for skeletonizing and computing at least one of end points and nodes for the polygon approximation of the cell.

17. The computer program product of claim 16, wherein $d_{TH}=c^*A$, where A is the area of the cell and c is a constant.

18. The computer program product of claim 17, wherein 1/50>c>1/100.

19. The computer program product of claim 18, wherein c =1/80.

20. A computer program product comprising a machine readable medium on which is provided program instructions for correlating a cell's shape with a biological condition of the cell, the instructions comprising:

(a) code for providing a plurality of segmented images of fields of one or more cells, at least one of said fields having been treated with a biologically active agent and at least one of said fields being a control and having not been treated with the biologically active agent, for each field, the code comprising:
  code for receiving a first image of a field of one or more cells in which a reference cell component of one or more cells is identified by a reference cell component marker image parameter,
  code for receiving a second image of the field of one or more cells in which at least one cell shape-indicative marker of the one or more cells is identified by a cell shape-indicative marker image parameter, and
  code for processing the first image in conjunction with the second image such that individual cell boundaries for the one or more cells in the field are identified;

for each of one or more of the cells in the plurality of segmented cell images, (b) code for selecting two endpoints defining two parts of the boundary of said cell;

(c) for each part of said cell boundary, code for computing the distance from each point on the part of the cell boundary to a line between said endpoints;

(d) code for determining a point $d_{MAX}$ on the portion of the boundary, said point $d_{MAX}$ being maximally distant from the line;

(e) code for comparing the distance from the point $d_{MAX}$ to a predetermined threshold distance value, $d_{TH}$;

(f) where $d_{MAX}$ is greater than $d_{TH}$, code for discarding the line between the endpoints, code for using point $d_{MAX}$ as a new endpoint together with one of the original endpoints to separate the part into two new parts, and code for repeating (c) and following;

(g) where $d_{MAX}$ is less than $d_{TH}$, code for using the line as a side of a polygon approximating the cell shape until a polygon approximating the shape of the cell is complete;

(h) code for skeletonizing and computing at least one of end points and nodes for the polygon approximation of the cell; and (i) code for comparing the computations of the at least one of end points and nodes for the polygon approximation of the cell to identify significant differences between the treated and control fields of one or more cells.

21. The computer program product of claim 20, wherein said code for computing of at least one of end points and nodes for the polygon approximation of the cell comprises code for quantifying the at least one of end points and nodes for the polygon approximation of the cell.

22. The computer program product of claim 20, wherein $d_{TH}=c*A$, where A is the area of the cell and c is a constant.

23. The computer program product of claim 22, wherein $1/50 > c > 1/100$.

24. The computer program product of claim 23, wherein $c = 1/80$.

* * * * *